US009645154B2

(12) United States Patent
Takagi et al.

(10) Patent No.: US 9,645,154 B2
(45) Date of Patent: May 9, 2017

(54) METHOD FOR DETECTING CANCER CELL

(75) Inventors: Hidenori Takagi, Kyoto (JP); Hiroshi Ito, Kyoto (JP); Masahiro Kozuka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 69 days.

(21) Appl. No.: 13/995,585

(22) PCT Filed: Dec. 22, 2011

(86) PCT No.: PCT/JP2011/079912
§ 371 (c)(1),
(2), (4) Date: Jul. 17, 2013

(87) PCT Pub. No.: WO2012/086802
PCT Pub. Date: Jun. 28, 2012

(65) Prior Publication Data
US 2013/0288273 A1 Oct. 31, 2013

(30) Foreign Application Priority Data
Dec. 24, 2010 (JP) ................. 2010-288936

(51) Int. Cl.
*G01N 33/72* (2006.01)
*G01N 33/58* (2006.01)
*G01N 33/574* (2006.01)

(52) U.S. Cl.
CPC ......... *G01N 33/582* (2013.01); *G01N 33/574* (2013.01); *G01N 33/72* (2013.01)

(58) Field of Classification Search
CPC .................................................. G01N 33/574
See application file for complete search history.

(56) References Cited

U.S. PATENT DOCUMENTS

| | | | |
|---|---|---|---|
| 6,034,267 A | 3/2000 | Gierskcky et al. | |
| 6,207,136 B1 | 3/2001 | Matsuoka | |
| 6,365,362 B1 | 4/2002 | Terstappen et al. | |
| 6,492,420 B2 | 12/2002 | Gierskcky et al. | |
| 6,645,731 B2 | 11/2003 | Terstappen et al. | |
| 6,992,107 B1 | 1/2006 | Gierskcky et al. | |
| 7,247,655 B2 | 7/2007 | Gierskcky et al. | |
| 7,287,646 B2 | 10/2007 | Gierskcky et al. | |
| 7,335,684 B2 | 2/2008 | Gierskcky et al. | |
| 7,530,461 B2 | 5/2009 | Gierskcky et al. | |
| 7,563,819 B1 | 7/2009 | Klaveness et al. | |
| 7,850,008 B2 | 12/2010 | Gierskcky et al. | |
| 8,410,172 B2 | 4/2013 | Gierskcky et al. | |
| 2001/0018192 A1 | 8/2001 | Terstappen et al. | |
| 2002/0009759 A1 | 1/2002 | Terstappen et al. | |
| 2002/0172987 A1 | 11/2002 | Terstappen et al. | |
| 2002/0183386 A1 | 12/2002 | Gierskcky et al. | |
| 2003/0129676 A1 | 7/2003 | Terstappen et al. | |
| 2004/0072269 A1 | 4/2004 | Rao et al. | |
| 2004/0106679 A1 | 6/2004 | Klaveness et al. | |
| 2007/0203027 A1 | 8/2007 | Tachiya et al. | |
| 2007/0224120 A1 | 9/2007 | Nakamura et al. | |
| 2008/0064752 A1 | 3/2008 | Braenden et al. | |
| 2008/0076139 A1 | 3/2008 | Singh | |
| 2008/0108701 A1 | 5/2008 | Okura et al. | |
| 2008/0188558 A1 | 8/2008 | Godal et al. | |
| 2008/0261829 A1 | 10/2008 | Harvey et al. | |
| 2009/0035792 A1 | 2/2009 | Singh et al. | |
| 2009/0123054 A1* | 5/2009 | Bodmer et al. | 382/134 |
| 2010/0004477 A1 | 1/2010 | Tachiya | |
| 2011/0125012 A1 | 5/2011 | Braenden et al. | |
| 2011/0250588 A1 | 10/2011 | Sato et al. | |
| 2012/0172227 A1 | 7/2012 | Tachiya et al. | |
| 2013/0066256 A1 | 3/2013 | Godal et al. | |

FOREIGN PATENT DOCUMENTS

| | | |
|---|---|---|
| EP | 0820432 B1 | 6/2001 |
| EP | 1797903 A1 | 6/2007 |
| JP | 06-109730 A | 4/1994 |
| JP | 07-035754 A | 2/1995 |
| JP | 07-104350 B2 | 11/1995 |
| JP | 08-320321 A | 12/1996 |
| JP | 09-176050 A | 7/1997 |
| JP | 09-176179 A | 7/1997 |
| JP | 10-505673 A | 6/1998 |
| JP | 10-253623 A | 9/1998 |
| JP | 11-012197 A | 1/1999 |
| JP | 11-171852 A | 6/1999 |
| JP | 11-246586 A | 9/1999 |
| JP | 2958447 B2 | 10/1999 |
| JP | 2989429 B2 | 12/1999 |
| JP | 2001-041959 A | 2/2001 |
| JP | 2001-501970 A | 2/2001 |
| JP | 3200607 B2 | 8/2001 |
| JP | 2002-529495 A | 9/2002 |

(Continued)

OTHER PUBLICATIONS

Gross et al, PNAS, 92:537-541, 1995.*
Ziegler et al, Lasers Surg Med, 43:548-56, Sep 2011, IDS filed on May 19, 2014.*
Nagrath et al (Nature 450:1235-1241, 2007.*
O'Neil et al, Mol Imaging Biol 7:388-392, 2005.*
Ziegler et al., "Fluorescence Detection and Depletion of T47D Breast Cancer Cells from Human Mononuclear Cell-Enriched Blood Preparations by Photodynamic Treatment: Basic In Vitro Experiments Towards the Removal of Circulating Tumor Cells," Lasers in Surgery and Medicine, 43: 548-556 (2011).
Egawa-Takata et al., "Early reduction of glucose uptake after cisplatin treatment is a marker of cisplatin sensitivity in ovarian cancer," Cancer Sci., 101: 2171-2178 (2010).

(Continued)

*Primary Examiner* — Lei Yao
(74) *Attorney, Agent, or Firm* — Morgan, Lewis & Bockius LLP

(57) ABSTRACT

A method for detecting a cancer cell, including: contacting in vitro a peripheral blood-containing sample including test cells and a labeling substance; allowing the test cells to incorporate the labeling substance to label the test cells; and detecting, as a cancer cell, a cell showing a higher degree of labeling with the labeling substance than that shown by a normal cell in the peripheral blood-containing sample.

10 Claims, 8 Drawing Sheets

(56) References Cited

FOREIGN PATENT DOCUMENTS

| | | | |
|---|---|---|---|
| JP | 2003-517819 A | 6/2003 |
| JP | 2003-526637 A | 9/2003 |
| JP | 2004-505040 A | 2/2004 |
| JP | 2004-505105 A | 2/2004 |
| JP | 2005-501050 A | 1/2005 |
| JP | 2005-132766 A | 5/2005 |
| JP | 2005-517904 A | 6/2005 |
| JP | 2005-241389 A | 9/2005 |
| JP | 2005-314360 A | 11/2005 |
| JP | 2006-124372 A | 5/2006 |
| JP | 2006-208399 A | 8/2006 |
| JP | 3834326 B2 | 10/2006 |
| JP | 2007-015937 A | 1/2007 |
| JP | 2007-015938 A | 1/2007 |
| JP | 3955093 B2 | 8/2007 |
| JP | 2007-530523 A | 11/2007 |
| JP | 2007-536207 A | 12/2007 |
| JP | 2008-044882 A | 2/2008 |
| JP | 2008-519261 A | 6/2008 |
| JP | 2008-519812 A | 6/2008 |
| JP | 2009-543089 A | 12/2009 |
| JP | 2010-504532 A | 2/2010 |
| JP | 4417865 B2 | 2/2010 |
| JP | 2010-513363 A | 4/2010 |
| JP | 2010-515714 A | 5/2010 |
| JP | 4630087 B | 2/2011 |
| JP | 4719483 B2 | 7/2011 |
| JP | 4869937 B2 | 2/2012 |
| JP | 4934292 B2 | 5/2012 |
| JP | 4934293 B2 | 5/2012 |
| JP | 4989153 B2 | 8/2012 |
| JP | 5010088 B2 | 8/2012 |
| JP | 5034032 B2 | 9/2012 |
| JP | 5134370 B2 | 1/2013 |
| JP | 5154557 B2 | 2/2013 |
| JP | 5164565 B2 | 3/2013 |
| JP | 5265855 B2 | 8/2013 |
| WO | 02/10120 A1 | 2/2002 |
| WO | 2005/092838 A1 | 10/2005 |
| WO | 2005/105708 A1 | 11/2005 |
| WO | 2006/051269 A1 | 5/2006 |
| WO | 2008/036802 A2 | 3/2008 |
| WO | 2010/071114 A1 | 6/2010 |

OTHER PUBLICATIONS

Millon et al., "Uptake of 2-NBDG as a method to monitor therapy response in breast cancer cell lines," Breast Cancer Research and Treatment (2010).
Cai et al., "2-NBDG Fluorescence Imaging of Hypermetabolic Circulating Tumor Cells in Mouse Xenograft model of Breast Cancer," Journal of Fluorescence (2012).
Office Action issued in related Chinese Patent Application No. 201180061918.1 dated Feb. 17, 2014.
Schirrmacher et al., "Quantitative Determination of Disseminated Tumor Cells by [3H]Thymidine Incorporation in Vitro and by Agar Colony Formation," Cancer Research, 42: 660-666 (1982).
Tamemasa et al., "Accumulations in Tumours of 99Tcm-Labelled Sulphur-Containing Amino Acids and Sugars," Radiopharm Label Compd. 281-290 (1985).
Peng et al., "5-Aminolevulinic Acid-Based Photodynamic Therapy," Cancer, 79: 2282-2308 (1997).
Extended European Search Report issued in corresponding European Patent Application No. 11850491.9 dated Nov. 20, 2014.
Office Action issued in Chinese Patent Application No. 201180061918.1 dated Sep. 2, 2014 (partial translation).
Teng et al., "The Study of Fluorescence Characteristic of Rat Brain C6 Glioma After Administration of 5-aminolevulinic Acid," Harbin Scientific and Technological Research Project (No. 2007AA3CS083-2): China Academic Journal Electronic Publishing House, 6: 25-29 (2008).
Tamemasa et al., "Preferential Incorporation of Some 14C-Labeled D-Amino Acids into Tumor-Bearing Animals," Gann, 69: 517-523 (1978).
Endo, "Clinical Applications of Pet," The Journal of the Japan Medical Association, 134: 1749-1752 (2005) (see partial English translation).
Office Action issued in corresponding Japanese Patent Application No. 2012-549887 dated Jan. 5, 2016 (see partial English translation).
Office Action including Common Knowledge Evidence issued in corresponding Chinese Patent Application No. 201180061918.1 dated Feb. 23, 2017 (partial English translation).

* cited by examiner

Method for Detecting Cancer Cell

METHOD FOR DETECTING CANCER CELL

TECHNICAL FIELD

The invention relates to a method for detecting a cancer cell.

BACKGROUND ART

Japanese Patent No. 3,834,326 discloses a method in which cancer cell is isolated with immunobeads and detected by, for example, immunostaining with an antibody. Japanese Patent Application Laid Open (JP-A) No. 2001-41959 discloses a method for detecting a cancer cell, including contacting a liquid containing a cancer cell with a support having an immobilized ligand that specifically binds to the cancer cell, and labeling the cancer cell bound to the support. Other known methods for detecting a cancer cell include a method in which a cancer cell is separated from a normal cell according to the size thereof and detected by immunostaining, and a method in which a cancer cell is separated from a normal cell by density gradient centrifugation and detected by immunostaining. For example, Japanese Patent No. 3,867,968 discloses a method for detecting a cancer cell contained in blood, in which the cancer cell infected with an adenovirus to express a fluorescent protein is detected.

SUMMARY OF INVENTION

Technical Problem

However, the technique described in Japanese Patent No. 3,834,326 or other methods using immunostaining can only detect a cell expressing an antigen. Furthermore, a target antigen to be detected is required to be identified in advance, and only the cell having the target antigen can be detected. Methods utilizing a support having an immobilized ligand that specifically binds to a cancer cell, such as the technique disclosed in JP-A No. 2001-41959, require the preparation of such a support in advance. Further, the technique described in Japanese Patent No. 3,867,968 requires culturing in order to infect the cells with a virus, and therefore requires about 24 hours to conduct a fluorescence measurement.

Thus, an object of the invention is to provide a method for detecting a cancer cell in which a cancer cell in peripheral blood can be detected rapidly and simply.

Solution to Problem

The invention includes the following aspects.
<1> A method for detecting a cancer cell, the method including: contacting in vitro a peripheral blood-containing sample including test cells with a labeling substance; allowing the test cells to incorporate the labeling substance to label the test cells; and detecting, as a cancer cell, a cell among the test cells showing a higher degree of labeling with the labeling substance than that shown by a normal cell in the peripheral blood-containing sample.
<2> The method for detecting a cancer cell according to <1>, wherein the labeling substance includes a substance labeled with a fluorescent substance or a precursor of the fluorescent substance, and the detection includes determining a fluorescence intensity of the test cells labeled with the fluorescent substance.
<3> The method for detecting a cancer cell according to <1> or <2>, wherein the labeling substance includes a substance labeled with a fluorescent substance or a precursor of the fluorescent substance, and the detection includes determining at least one selected from the group consisting of a mean fluorescence intensity and a total fluorescence intensity of the test cells labeled with the fluorescent substance.
<4> The method for detecting a cancer cell according to any one of <1> to <3>, wherein the detection is performed further on the basis of a size of the test cells labeled with the fluorescent substance.
<5> The method for detecting a cancer cell according to any one of <1> to <4>, wherein the labeling substance includes at least one selected from the group consisting of a labeled sugar, a labeled amino acid, and a substance to be incorporated into the cells and metabolized to protoporphyrin IX.
<6> The method for detecting a cancer cell according to any one of <1> to <5>, wherein the labeling substance includes a labeled sugar and a labeled amino acid.
<7> The method for detecting a cancer cell according to any one of <1> to <6>, wherein the labeling substance includes a labeled sugar, and the labeled sugar includes a labeled monosaccharide.
<8> The method for detecting a cancer cell according to any one of <1> to <7>, wherein the labeling substance includes a labeled sugar, and the labeled sugar includes a fluorescently-labeled glucose derivative.
<9> The method for detecting a cancer cell according to any one of <1> to <8>, wherein the labeling substance includes a labeled amino acid, and the amino acid includes at least one selected from the group consisting of natural amino acids and non-natural amino acids.
<10> The method for detecting a cancer cell according to any one of <1> to <9>, wherein the labeling substance includes a labeled amino acid, and the amino acid includes at least one selected from the group consisting of neutral amino acids and acidic amino acids.
<11> The method for detecting a cancer cell according to any one of <1> to <10>, wherein the labeling substance includes a substance to be incorporated into the cells and metabolized to protoporphyrin IX, and the substance includes at least one selected from the group consisting of aminolevulinic acid and derivatives thereof.
<12> The method for detecting a cancer cell according to any one of <1> to <11>, wherein the labeling substance includes a substance to be incorporated into the cell and metabolized to protoporphyrin IX, and the substance includes at least one selected from the group consisting of salts of aminolevulinic acid or a derivative thereof, esters of aminolevulinic acid and derivative thereof and salts of the esters.
<13> The method for detecting a cancer cell according to any one of <1> to <12>, wherein the peripheral blood-containing sample including the test cells is hemolyzed.
<14> The method for detecting a cancer cell according to any one of <1> to <13>, the method further including contacting in vitro a cell type-distinguishing antibody with the peripheral blood-containing sample including the test cells.
<15> The method for detecting a cancer cell according to <14>, wherein the cell type-distinguishing antibody includes at least one selected from the group consisting of an anti-CD45 antibody and an anti-CD34 antibody.
<16> The method for detecting a cancer cell according to any one of <1> to <15>, wherein the contacting in vitro of the peripheral blood-containing sample including the test cells with the labeling substance is conducted in the presence of an iron ion and a reducing agent.

<17> The method for detecting a cancer cell according to any one of <1> to <16>, wherein the contacting in vitro of the peripheral blood-containing sample including the test cells with the labeling substance is conducted in the presence of at least one selected from the group consisting of an endocytosis inducing substance and a cell membrane protein-stabilizing ion.

<18> The method for detecting a cancer cell according to any one of <1> to <17>, wherein the contacting in vitro of the peripheral blood-containing sample including the test cells with the labeling substance is conducted using the labeling substance at a concentration of from 0.1 µM to 100 mM.

<19> The method for detecting a cancer cell according to any one of <1> to <18>, wherein the test cells are allowed to incorporate the labeling substance for labeling under a condition of from 1° C. to 42° C.

<20> The method for detecting a cancer cell according to any one of <1> to <19>, wherein the test cells are allowed to incorporate the labeling substance for labeling for from 1 minute to 5 hours.

<21> A kit for detecting a cancer cell, including a labeling substance and at least one selected from the group consisting of a cell type-distinguishing antibody and a washing solution.

Advantageous Effect of Invention

According to the invention, there can be provided a method for detecting a cancer cell in which a cancer cell in peripheral blood can be detected rapidly and simply.

DESCRIPTION OF EMBODIMENTS

Figure 1:
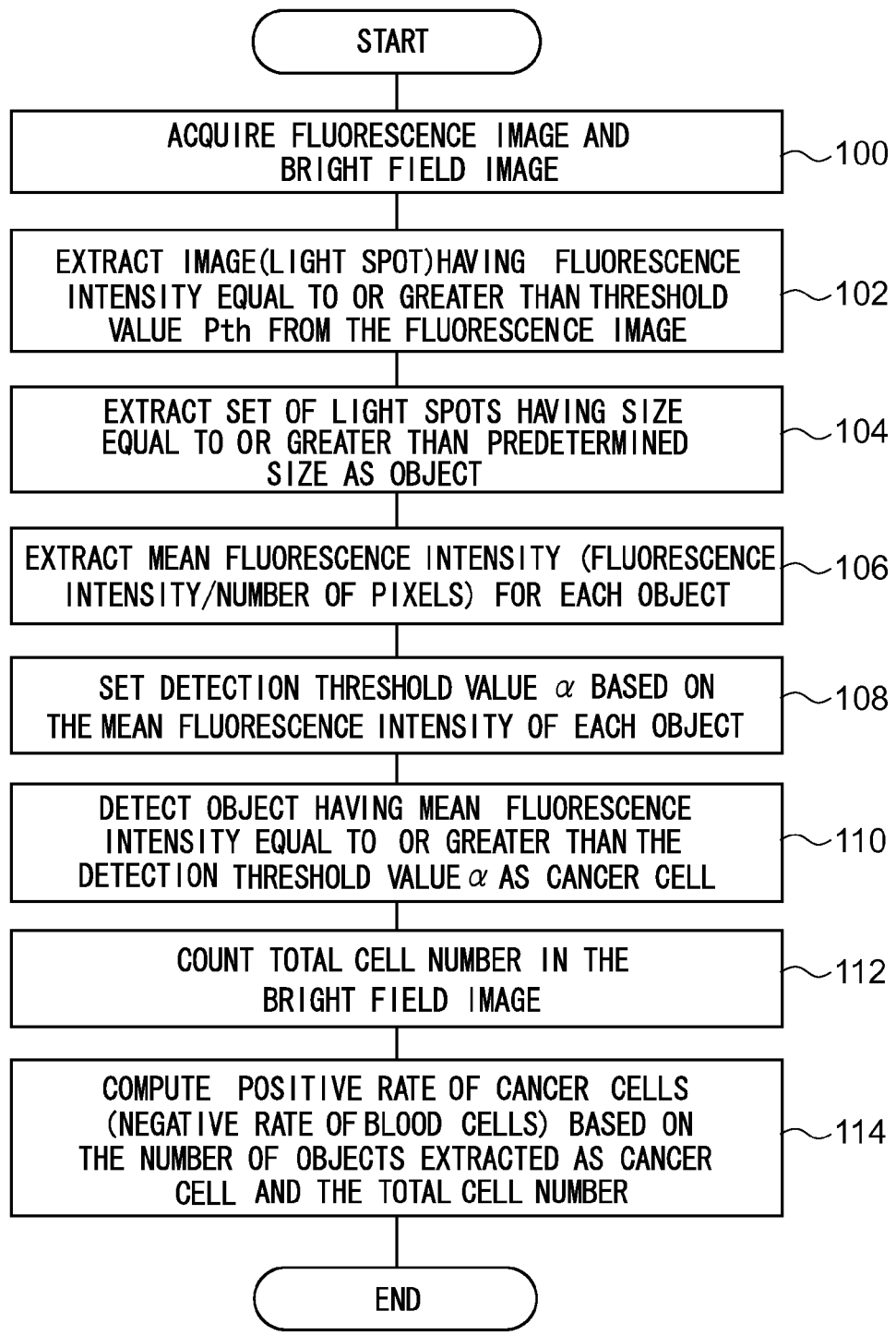
FIG. 1 is a flow chart illustrating the contents of an image processing procedure according to an embodiment of the invention.

The method for detecting a cancer cell according to the invention includes: contacting in vitro a peripheral blood-containing sample including test cells with a labeling substance; allowing the test cells to incorporate the labeling substance to label the test cells; and detecting, as a cancer cell, a cell among the test cells showing a higher degree of labeling with the labeling substance than that shown by a normal cell in the peripheral blood-containing sample.

In the method for detecting a cancer cell according to the invention, the labeling substance is allowed to be incorporated into the test cells of the peripheral blood cells in vitro, and a cell showing a higher degree of labeling than that shown by a normal cell is detected as a cancer cell. In general, cancer cells can incorporate larger amounts of labeling substances than normal cells, since cancer cells have a higher metabolic rate than that of normal cells. Furthermore, the degree of labeling is different between cancer cells and normal cells, since cancer cells have a different metabolic pathway than that of normal cells.

Therefore, according to the invention, whether the test cell in peripheral blood cells is a cancer cell or a normal cell can be rapidly and simply determined based on the degree of labeling with the labeling substance, without depending on the presence of a cancer cell surface antigen and without preparing a specific support.

The term "step" as used herein includes not only a separate step but also a step that is not clearly distinguished from other steps as long as the desired effect of the step is obtained therefrom.

As used herein, the notation "to" expressing a numerical range indicates a range including the numerical values before and after "to", as the minimum value and the maximum value, respectively.

As regard to the amount of a component of a composition, when plural substances corresponding to the same component exist in the composition, the amount of the component used herein refers to a total amount of the plural substances in the composition unless otherwise specified.

The term "false-positive results" as used herein means that a non-cancer cell is detected in the detection of a cancer cell.

The term "peripheral blood-containing sample" as used herein means a sample containing a peripheral blood.

The invention is described below.

The method for detecting a cancer cell according to the invention includes: contacting in vitro the peripheral blood-containing sample including test cells with a labeling substance (hereinafter, also referred to as a "contacting step"); allowing the test cells to incorporate the labeling substance (hereinafter, also referred to as a "incorporation step") and optionally metabolized therein, thereby labeling the test cells (hereinafter, also referred to as a "labeling step"); and detecting, as a cancer cell, a cell among the test cells showing a higher degree of labeling with the labeling substance than that shown by a normal cell in the peripheral blood-containing sample (hereinafter, also referred to as a "detection step").

In this way, the presence of a cancer cell in the peripheral blood-containing sample including a peripheral blood sample can be rapidly and simply detected based on the degree of labeling with the labeling substance.

The test cells includes a population of cells circulating in peripheral blood. In general, a cancer cell among the test cells is sometimes called a circulating tumor cell (CTC) and thought to be highly metastatic, but the cancer cell is not limited to this.

In the invention, the cancer cell to be tested is not specifically limited as long as it is a cancer cell that can be present in peripheral blood. Examples of the cancer include, but not limited to, brain tumor, glioma, pituitary adenoma, acoustic neurinoma, retinoblastoma, uveal malignant melanoma, epipharyngeal carcinoma, mesopharyngeal cancer, hypopharyngeal cancer, laryngeal cancer, lung cancer, thymoma, mesothelioma, breast cancer, gastric cancer, esophageal cancer, colon cancer, hepatocellular carcinoma, cholangiocarcinoma, gallbladder cancer, pancreatic cancer, pancreatic endocrine tumor, penile cancer, renal pelvic and ureteral cancer, renal cell carcinoma, testis tumor (orchioncus), prostate cancer, bladder cancer, vulvar cancer, cervical cancer, uterine corpus cancer, endometrial cancer, uterine sarcoma, vaginal cancer, ovarian cancer, ovarian germ cell tumor, skin cancer, intraepidermal carcinoma, squamous cell carcinoma, basal cell carcinoma, malignant melanoma, mycosis fungoides, malignant bone tumor, soft tissue sarcoma, hereditary tumor, familial tumor, carcinoma of unknown origin, acute myeloid leukemia, acute lymphocytic leukemia, myelodysplastic syndrome, chronic myeloid leukemia/chronic myeloproliferative disorder, adult T cell leukemia-lymphoma, chronic lymphocytic leukemia, small lymphocytic lymphoma and multiple myeloma.

In the invention, the labeling substance may be any substance as long as it is incorporated into a cancer cell and enables the detection of the cancer cell at the detection step described below.

The labeling substance may be any substance as long as it is detectable at the time of detection, and may be a substance that is detectable before being incorporated into a cancer cell (for example, a substance labeled with a fluorescent substance) or a substance that becomes detectable after being incorporated into a cancer cell (for example, a precursor of a fluorescent substance).

Examples of the substance that is detectable before being incorporated into a cancer cell include a sugar labeled with a known labeling substance (labeled sugar), an amino acid labeled with a known labeling substance (labeled amino acid), a nucleic acid labeled with a known labeling substance (labeled nucleic acid), acetic acid labeled with a known labeling substance (labeled acetic acid), choline labeled with a known labeling substance (labeled choline), and folic acid labeled with a known labeling substance (labeled folic acid).

Examples of the substance that becomes detectable after being incorporated into a cancer cell include a substance to be incorporated into a cell and metabolized to protoporphyrin IX.

Further, as the labeling substance, the labeled sugar and the labeled amino acid may be used in combination, in view of expanding the ranges of the types of target cancer cells and improving detection sensitivity for the detecting method according to the invention.

The labeled sugar in the invention may be any substance obtained by labeling a sugar, which is incorporated into a cell and is thereafter available as a nutrient that can act as an energy source for the cell, using a method described below.

Examples of the sugar include a monosaccharide, a disaccharide, or an oligosaccharide including about 3 to 10 sugar units. Further, the sugar may be monosaccharide, since the monosaccharide is a nutrient that can act as an energy source for cells, and the monosaccharide is incorporated into cells constitutively and incorporated in a sufficient amount even in the case of short-term culture. Sugars other than monosaccharides may be modified into forms capable of being incorporated into cells. Specific examples of the sugar include glucose, deoxyglucose, glucosamine, galactose, mannose, fructose, arabinose, sucrose, lactose and maltose. In view of its incorporation into cells, glucose may be used.

Any labels may be used for labeling the sugar without any restrictions as long as they are commonly used in the art, and a labeling substance generally used for labeling a biological substance may be used. Examples of the labeling substance include an enzyme that catalyzes chromogenic reaction, a fluorescent substance, a radioisotope and biotin. For microscopic detection, an enzyme, a fluorescent substance and a chemiluminescent substance are preferable. Among these, labeling with a fluorescent substance is preferable. Labeling with a fluorescent substance enables the simple detection, for example, based on a fluorescence intensity.

Examples of the fluorescent substance include, but not limited to, fluorescent proteins such as Alexa Fluor dye and green fluorescent protein (GFP); fluorescein derivatives such as fluorescein isothiocyanate (FITC); and fluorescent dyes such as rhodamine, phycoerythrin (PE), phycocyanin (PC), Cy dye, TexasRed, allophycocyanin (APC), quantum dot, Aminomethylcoumarin Acetate (AMCA), Marina Blue, Cascade Blue, Cascade Yellow, Pacific Blue, SPRD, tetramethylrhodamine isothiocyanate (TRITC), R110, mCIB, CellTracker dye, CFSE, JC-1, PKH, DCFH-DA, DHR, FDA, Calcein AM, a nitrobenzoxadiazole (NBD) group, a dimethylamino sulfonylbenzoxadiazole (DBD) group, benzoacridine (Bacd), acridine (Acd), dansyl (Dns), 7-Dimethylaminocoumarinch-4-acetic acid (DMACA), 5-((2-Aminoethyl)amino)naphthalene-1-sulfonic acid (EDANS), naphthalene (Nap), anthracene (Ant) and protoporphyrin IX.

Examples of the precursor of the fluorescent substance include a substance to be incorporated into a cell and generates protoporphyrin IX as described below.

Examples of the chemiluminescent substance include luminol, isoluminol, acridinium derivatives, lophine, lucigenin and peroxalic acid esters.

As a substrate for the enzyme, diaminobenzidine or the like may be used.

In a case in which biotin is used as the labeling substance, an avidin-conjugated enzyme or a fluorescent substance may be further attached for detection. Any conventional method may be used for labeling with these label substances.

The labeling substance may be a labeling substance having a N-(7-nitrobenz-2-oxa-1,3-diazol-4-yl)amino group as fluorescent chromophore.

In view of its efficient incorporation into the test cells, the labeled sugar may be a fluorescent-labeled glucose or a fluorescently-labeled glucose derivative. Further, in view of stable detection of a cancer cell, the labeled sugar may be a D-glucose derivative having a N-(7-nitrobenz-2-oxa-1,3-diazol-4-yl)amino group as a fluorescent chromophore.

Examples of the D-glucose derivative include 2-[N-(7-nitrobenz-2-oxa-1,3-diazol-4-yl)amino]-2-deoxy-D-glucose (2-NBDG, Yamada K. et al., J. Biol. Chem. 275:22278-22283, 2000), and 6-[N-(7-nitrobenz-2-oxa-1,3-diazol-4-yl) amino]-6-deoxy-D-glucose (6-NBDG: Speizer L. et al., Biochim. Biophys. Acta 815:75-84, 1985).

These labeled sugars may be used singly, or in combination of two or more kinds thereof.

The amino acid of the labeled amino acid in the invention may be a natural amino acid or a non-natural amino acid.

Examples of the natural amino acid include neutral amino acids such alanine (Ala), glycine (Gly), valine (Val), leucine (Leu), isoleucine (Ile), Phenylalanine (Phe), thyrosin (Tyr), tryptophan (Trp), proline (Pro), serine (Ser), threonine (Thr), cysteine (Cys), methionine (Met), asparagine (Asn), and glutamine (Gln); acidic amino acids such as aspartic acid (Asp) and glutamic acid (Glu); basic amino acids such as lysine (Lys), arginine (Arg) and histidine (His).

The non-natural amino acid may be any amino acid derivative as long as it is transported into a cell by an amino acid transporter similarly to the natural amino acid.

Examples of the non-natural amino acid include, but not limited to, α-aminocyclobutane carboxylic acid (ACBC), α-aminocyclopetane carboxylic acid (ACPC) and α-aminoisobutyric acid (AIB).

Similar to the natural amino acid, the non-natural amino acid can be classified into a neutral amino acid, an acidic amino acid or a basic amino acid according to its chemical property, and can be used as the amino acid for the invention according to the classification From the viewpoint of reducing the false-positive rate, the amino acid may be an amino acid selected from the group consisting of neutral amino acids and acidic amino acids.

From the view point of improving positive rate, the amino acid may be an amino acid selected from the group consisting of neutral amino acids and basic amino acids.

Further, from the view point of reducing the false-positive rate and improving positive rate, the amino acid may be an amino acid selected from the group consisting of neutral amino acids.

The amino acid may be labeled with a similar labeling substance to that used for the labeled sugar. In view of its efficient incorporation into the test cells, the amino acid is preferably labeled with, but not limited to, benzoacridine (Bacd), acridine (Acd), 7-Dimethylaminocoumarin-4-acetic acid (DMACA), 5-((2-Aminoethyl)amino)naphthalene-1-sulfonic acid (EDANS), naphthalene (Nap) or anthracene (Ant).

These labeled amino acids may be used singly, or in combination of two or more kinds thereof.

Examples of the precursor of the fluorescent substance in the invention include a "substance to be incorporated into a cell and generates protoporphyrin IX". Examples of the "substance to be incorporated into a cell and generates protoporphyrin IX" include aminolevulinic acid (5-amino-4-oxopentanoic acid) or a derivative thereof. Here, the "substance to be incorporated into a cell and generates protoporphyrin IX" is also called "aminolevulinic acid or a derivative thereof."

Examples of aminolevulinic acid or a derivative thereof include aminolevulinic acid or a derivative thereof, salts of aminolevulinic acid or a derivative thereof, esters of aminolevulinic acid or a derivative thereof, and salts of the esters.

Specific examples thereof include aminolevulinic acid and derivatives thereof such as aminolevulinic acid, methyl aminolevulinate, ethyl aminolevulinate, propyl aminolevulinate, hexyl aminolevulinate, heptyl aminolevulinate and octyl aminolevulinate; esters of aminolevulinic acid and derivatives thereof such as aminolevulinic acid methyl esters, aminolevulinic acid ethyl esters, aminolevulinic acid propyl esters, aminolevulinic acid hexyl ester, aminolevulinic acid heptyl esters and aminolevulinic acid octyl esters; salts of aminolevulinic acid or a derivative thereof such as hydrochlorides, sulfonates, ester phosphates, ester sulfonates, phosphates, nitrates and sulfates of aminolevulinic acid or a derivative thereof; and salts of the esters.

Examples of the commercial products thereof include, but not limited to, aminolevulinic acid 5-AMINOLEVULINATE HYDROCHLORIDE (trade name, manufactured by Cosmo Bio Co., Ltd.), and aminolevulinic acid methyl ester 5-AMINOLEVULINIC ACID METHYL ESTER HYDROCHLORIDE (trade name, manufactured by Tokyo Chemical Industry Co., Ltd.).

As the labeling substance, the labeled sugar, the labeled amino acid or the substance to be incorporated into a cell and metabolized to protoporphyrin IX may be used singly, or in combination of two or more kinds thereof.

As the labeling substance, the labeled sugar and the labeled amino acid may be used in combination. When the labeled sugar and labeled amino acid are used in combination, the possibility of being affected by the incorporation rate of the labeled sugar or labeled amino acid, which are thought to be varied depending on the types of cancer cells, can be reduced. This enables a simple detection of a cancer cell, and detection of various types of cancer cells.

In order to simplify the detection method, the labeling substance used for labeling the sugar may have similar fluorescent properties to the labeling substance used for labeling the amino acid. The combination of labeling substances having similar fluorescent properties may be any combination as long as the difference in the maximum absorption wavelength is 75 nm or less and the difference in the maximum fluorescence wavelength is 150 nm or less. Examples of the combinations include, but not limited to, combinations of a nitrobenzoxadiazole (NBD) group and a benzoacrydony (Bacd) group, a NBD group and fluorescein isothiocyanate (FITC), a NBD group and Alexa Fluor dye having similar fluorescent properties with the NBD group, a NBD group and green fluorescent protein (GFP), a NBD group and Calcein AM, a NBD group and FDA, a NBD group and quantum dot having similar fluorescent properties with the NBD group, a NBD group and CellTracker dye having similar fluorescent properties with the NBD group, a NBD group and A43, a NBD group and Fam, a Bacd group and FITC, a Bacd group and Alexa Fluor dye having similar fluorescent properties with the Bacd group, a Bacd group and GFP, a Bacd group and Calcein AM, a Bacd group and quantum dot having similar fluorescent properties with the Bacd group, a Bacd group and CellTracker dye having similar fluorescent properties with the Bacd group, a Bacd group and A43, a Bacd group and Fam, FITC and Alexa Fluor dye having similar fluorescent properties with FITC, FITC and GFP, FITC and Calcein AM, FITC and quantum dot having similar fluorescent properties with FITC, FITC and CellTracker dye having similar fluorescent properties with FITC, FITC and A43, FITC and Fam, GFP and Alexa Fluor dye having similar fluorescent properties with GFP, Calcein AM and Alexa Fluor dye having similar fluorescent properties with Calcein AM, A43 and Alexa Fluor dye having similar fluorescent properties with A43, Fam and Alexa Fluor dye having similar fluorescent properties with Fam, Pacific Blue and Cascade Blue, Pacific Blue and Hoc, Pacific Blue and Alexa Fluor dye having similar fluorescent properties with Pacific Blue, Pacific Blue and quantum dot having similar fluorescent properties with Pacific Blue, phycoerythrin (PE) and tetramethylrhodamine isothiocyanate (TRITC), PE and Cy dye having similar fluorescent properties with PE, PE and Alexa Fluor dye having similar fluorescent properties with PE, PE and quantum dot having similar fluorescent properties with PE, PE and CellTracker dye having similar fluorescent properties with PE, PE and rhodamine, PE and Tmr, TRITC and rhodamine, TRITC and Tmr, TRITC and Cy dye having similar fluorescent properties with TRITC, TRITC and Alexa Fluor dye having similar fluorescent properties with TRITC, TRITC and quantum dot having similar fluorescent properties with TRITC, TRITC and CellTracker dye having similar fluorescent properties with TRITC, rhodamine and Tmr, rhodamine and CellTracker dye having similar fluorescent properties with rhodamine, rhodamine and quantum dot having similar fluorescent properties with rhodamine, rhodamine and Cy dye having similar fluorescent properties with rhodamine, Tmr and CellTracker dye having similar fluorescent properties with Tmr, Tmr and quantum dot having similar fluorescent properties with Tmr, Tmr and Cy dye having fluorescent properties with Tmr, allophycocyanin (APC) and Alexa Fluor dye having similar fluorescent properties with APC, APC and quantum dot having similar fluorescent properties with APC, APC and CellTracker dye having similar fluorescent properties with APC, APC and Cy dye having similar fluorescent properties with APC, Aminomethylcoumarin Acetate (AMCA) and Alexa Fluor dye having similar fluorescent properties with AMCA, AMCA and quantum dot having similar fluorescent properties with AMCA, AMCA and Cy dye having similar fluorescent properties with AMCA, Alexa Fluor dye and quantum dot having similar fluorescent properties with Alexa Fluor dye, Alexa Fluor dye and CellTracker dye having similar fluorescent properties with Alexa Fluor dye, and quantum dot and CellTracker dye having similar fluorescent properties with quantum dot.

In order to simplify the detection step described below, the labeling substance for labeling the sugar and the labeling substance for labeling the amino acid may be the same labeling substance.

A peripheral blood sample to be tested in the invention may a blood obtained from a subject. The subject is not specifically limited, and may be human, primates such as monkey; rodents such as mouse and rat; domestic animals such as swine, bovine and equine; pet animals such as canine, feline and rabbit.

The peripheral blood sample may be any sample collected from venous blood by a common collection method. The peripheral blood sample may be diluted with an appropriate diluent to a predetermined concentration in order to adjust the density. The diluent for the peripheral blood sample that may be used for diluting the peripheral blood is preferably a diluent having an osmotic pressure close to that of cells, and is not particular limited as long as it is a commonly used diluent. Examples thereof include physiological saline, phosphate-buffered saline (PBS), Tris-HCl buffer, citrate-phosphate buffer and citrate buffer. In general, a pH value of the diluent for a peripheral blood sample may be any value within the range of from pH 5 to pH 9.

The peripheral blood sample may be concentrated in order to increase a cancer cell density before the contacting with the labeling substance. For a method of concentration, any commonly used method such as centrifugation and filter separation may be used. In this manner, the test sample can be prepared as a sample having a higher cancer cell density.

The peripheral blood sample may be hemolyzed before the contacting step. By hemolyzing the peripheral blood sample, erythrocytes constituting the majority of the blood cell components can be removed. This reduces a false-positive rate caused by the presence of erythrocytes, whereby a cancer cell can be detected simply with improved sensitivity.

Any known method may be used for the hemolyzing treatment. For example, a blood cell fraction that has been separated may be treated using a hemolyzing reagent. The conditions for treating the blood cell fraction with a hemolyzing reagent vary depending on the types of the hemolyzing reagent, and can be appropriately selected by a person skilled in the art.

Any known reagent may be used as the hemolyzing reagent, and examples thereof including ammonium chloride, sodium chloride, ammonium oxalate, saponin, surfactants such as sodium lauryl sulfate (SDS), and other commercially available hemolyzing reagents such as IMMUNOPREP (Beckman Coulter, Inc.), IMMUNO-LYSE (Beckman Coulter, Inc.) and BD FACS (registered trademark) LYSING SOLUTION (Becton, Dickinson and Company). In view of the incorporation efficiency of the labeling substance into the test cells and the labeling efficiency of the labeling substance, ammonium chloride, saponin and a commercially available hemolyzing reagent having a weak hemolyzing activity may be used as the hemolyzing reagent.

The hemolyzing reagent may be added to the peripheral blood sample such that the concentration (final concentration) of the hemolyzing reagent is from 0.01% by mass to 10% by mass. The amount (final concentration) of the hemolyzing reagent is preferably in the range of from 0.05% by mass to 5% by mass, from the viewpoint of reducing the false-positive rate. The amount (final concentration) of the hemolyzing reagent is more preferably in the range of from 0.1% by mass to 1% by mass, from the viewpoints of reducing the false-positive rate, and simplifying the detection of cancer cells.

The method of contacting the peripheral blood-containing sample with the labeling substance in the contacting step is not particularly limited. In general, the labeling substance having a predetermined concentration may be added to the peripheral blood-containing sample (hereinafter, also referred to as "the addition step").

For example, the labeling substance may be added to the peripheral blood-containing sample such that the labeling substance has a concentration (final concentration) of from 0.1 µM to 100 mM. It is preferable that the labeling substance is added to the peripheral blood-containing sample such that the labeling substance has a concentration (final concentration) of from 0.3 µM to 75 mM. It is more preferable that the labeling substance is added to the peripheral blood-containing sample such that the labeling substance has a concentration (final concentration) of from 1 µM to 50 mM.

In a case in which the labeling substance is the labeled sugar, the concentration (final concentration) of the labeled sugar used may be from 0.01 mM to 100 mM, in view of detection sensitivity of a cancer cell. The concentration (final concentration) of the labeled sugar used is preferably from 0.05 mM to 75 mM, from the viewpoints of detection sensitivity of a cancer cell and reducing the false-positive rate. The concentration (final concentration) of the labeled sugar used is more preferably from 0.1 mM to 50 mM, from the viewpoints of detection sensitivity of a cancer cell and reducing the false-positive rate.

In a case in which the labeling substance is the labeled amino acid, the concentration (final concentration) of the labeled amino acid used may be from 0.1 µM to 100 mM, in view of detection sensitivity of a cancer cell. The concentration (final concentration) of the labeled amino acid used is preferably from 0.5 µM to 50 mM, from the viewpoints of detection sensitivity of a cancer cell and reducing the false-positive rate. The concentration (final concentration) of the labeled amino acid used is more preferably from 1 µM to 10 mM, from the viewpoints of detection sensitivity of a cancer cell and reducing the false-positive rate.

In a case in which the labeling substance is aminolevulinic acid or a derivative thereof, the concentration (final concentration) of aminolevulinic acid or a derivative thereof used may be from 0.01 mM to 100 mM, in view of detection sensitivity of a cancer cell. The concentration (final concentration) of aminolevulinic acid or a derivative thereof used is preferably from 0.05 mM to 50 mM, from the viewpoints of detection sensitivity of a cancer cell and reducing the false-positive rate. The concentration (final concentration) of aminolevulinic acid or a derivative thereof used is more preferably from 0.1 mM to 10 mM, from the viewpoints of detection sensitivity of a cancer cell and reducing the false-positive rate.

In a case in which a combination of the labeled sugar and the labeled amino acid is used as the labeling substance, the concentration (final concentration) of the labeled sugar and the labeled amino acid used may be from 0.1 µM to 100 mM, in view of detection sensitivity of a cancer cell. The concentration (final concentration) of the labeled sugar and the labeled amino acid used is preferably from 0.3 µM to 75 mM, form the viewpoints of detection sensitivity of a cancer cell and reducing the false-positive rate. The concentration (final concentration) of the labeled sugar and the labeled amino acid used is more preferably from 1 µM to 50 mM, from the viewpoints of detection sensitivity of a cancer cell and reducing the false-positive rate.

In the addition step, the peripheral blood-containing sample including the test cells may be contacted in vitro with a cell type-distinguishing antibody.

By contacting the peripheral blood-containing sample including the test cells with the cell type-distinguishing antibody, various types of cells present in the peripheral blood sample can be individually labeled and recognized, thereby reducing the false-positive rate and simplifying the detection of cancer cells.

Any antibody may be used as the cell type-distinguishing antibody, as long as it is labeled with s labeling substance as used for labeling the sugar described above.

Any cell type-distinguishing antibody may be used as long as it can individually recognize and label various types of cells present in a population of the peripheral blood cells, and examples thereof include cell type-distinguishing antibodies used for reducing the false-positive rate, and cell type-distinguishing antibodies used in order to simplify the detection of cancer cells.

As the cell type-distinguishing antibody used for reducing the false-positive rate, any antibody recognizing a non-cancer cell in a blood cell fraction may be used. Examples thereof include an anti-CD45 antibody, an anti-CD34 antibody, an anti-CD3 antibody, an anti-CD4 antibody, an anti-CD14 antibody, an anti-CD20 antibody, an anti-CD36 antibody, an anti-CD41 antibody and an anti-CD309 antibody. For example, in view of the potential broad recognition of leucocytes, vascular endothelial cells, vascular endothelial cell precursors, undifferentiated leukocytes and hematopoietic cells, which are difficult to be removed by using a hemolyzing reagent, at least one selected from the group consisting of an anti-CD45 antibody and an anti-CD34 antibody may be used as the cell type-distinguishing antibody for reducing the false-positive rate.

As the cell type-distinguishing antibody in order to simplify the detection of cancer cells, any antibody known to specifically recognize various cancer cells may be used. Examples thereof include an anti-cytokeratin (CK) antibody, an anti-epithelial cell adhesion molecule (EpCAM) antibody, an anti-carcinoembryonic antigen (CEA) antibody, an anti-prostate specific antigen (PSA) antibody, an anti-mucin (MUC) antibody, an anti-p53 antibody, an anti-Sialyl Lewis X antibody, an anti-MAGE (Melanoma-associated antigen) antibody, an anti-MMP (Matrix metalloproteinase) antibody, an anti-α-fetoprotein (AFP) antibody, an anti-epidermal growth factor receptor (EGFR) antibody, an anti-epidermal growth factor receptor (EGFR) antibody, an anti-epidermal growth factor receptor (EGFR) antibody, an anti-HER2 antibody, an anti-HER3 antibody, an anti-folate receptor antibody, an anti-TROP-2 antibody, an anti-c-kit antibody, an anti-c-met antibody, an anti-CA-125 antibody, an anti-CA-19 antibody, an anti-E-cadherin antibody, an anti-N-cadherin antibody, an anti-estrogen receptor (ER) antibody, an anti-heat shock protein (HSP) antibody, an anti-insulin-like growth factor receptor (IGFR) antibody, an anti-Ki-67 antibody, an anti-Survivin antibody, an anti-vimentin antibody and an anti-telomerase reverse transcriptase (TERT) antibody. For example, in view of the potential broad spectrum of the detection of cancer cells, at least one selected from the group consisting of an anti-cytokeratin (CK) antibody, an anti-epithelial cell adhesion molecule (EpCAM) antibody, an anti-vimentin antibody and an anti-N-cadherin antibody may be used as the cell type-distinguishing antibody in order to simplify the detection of cancer cells.

These cell type-distinguishing antibodies may be used singly, or in combination of two or more kinds thereof.

In a case in which the labeling substance is aminolevulinic acid or a derivative thereof, the contacting step may be performed in the presence of an iron ion and a reducing agent.

It is assumed that, when the contacting step of the target cell with the aminolevulinic acid or a derivative thereof is conducted in the presence of the iron ion and the reducing agent, the iron ion is stabilized in the divalent state by the presence of the reducing agent. Therefore, the false-positive rate is thought to be reduced since protoporphyrin IX once generated is rapidly metabolized in normal cells.

Examples of the reducing agent include ascorbic acid, ascorbic acid stearic acid ester, tocopherol, lecithin, catechin, citric acid, oxalic acid, glucose, glutathione, erythorbic acid, dibutylated hydroxytoluene (BHT) and butylated hydroxyanisole. In view of the ability to stably maintain the iron ion in the divalent state in an aqueous solution, and the strong reducing ability and low cytotoxicity, it is preferable to use ascorbic acid, erythorbic acid, catechin, or citric acid. It is more preferable to use ascorbic acid.

In this case, the concentration of iron ions may be from 0.01 mM to 100 mM, and the concentration of ascorbic acid may be from 0.01 mM to 100 mM.

From the viewpoint of reducing the false-positive rate, it is preferable to use a divalent iron ion as the iron ion, and the concentration thereof may be from 0.05 mM to 50 mM while the concentration of ascorbic acid may be from 0.05 mM to 50 mM. From the viewpoint of reducing the false-positive rate, it is more preferable to use a divalent iron ion as the iron ion, and the concentration thereof may be from 0.1 mM to 10 mM while the concentration of ascorbic acid may be from 0.1 mM to 10 mM.

In a case in which the labeling substance is aminolevulinic acid or a derivative thereof, the contacting step may be performed in the presence of at least one selected from the group consisting of an endocytosis inducing substance and a cell membrane protein-stabilizing ion.

It is assumed that, when the step of contacting the target cell with aminolevulinic acid or a derivative thereof is conducted in the presence of at least one selected from the group consisting of the endocytosis inducing substance and the cell membrane protein stabilizing-ion, the incorporation of aminolevulinic acid or a derivative thereof into the target cell is promoted. In a case in which aminolevulinic acid or a derivative thereof is used, aminolevulinic acid or derivative thereof is required to be converted into protoporphyrin IX for the detection step. The target cell may be contacted and incubated with aminolevulinic acid or a derivative thereof. This promotes the incorporation of aminolevulinic acid, thereby reducing the contact (incubation) time of aminolevulinic acid or a derivative thereof with the target cell and improving the reactivity of aminolevulinic acid or a derivative thereof.

The endocytosis inducing substance is a substance for promoting the incorporation of substances into cells, and examples thereof include amphiphilic peptides, cationic lipids, cholesterol, neutral phospholipids and neutral lipids.

Examples of commercially available products thereof include, but not limited to, the amphiphilic peptide ENDO-PORTER (trade name, manufactured by Gene Tools, LLC), the amphiphilic peptide ENDO-PORTER AQUEOUS (trade name: manufactured by Gene Tools, LLC), the cationic lipid LIPOFECTIN REAGENT (trade name: manufactured by Invitrogen), the cationic lipid LIPOFECTAMINE 2000 REAGENT (trade name: manufactured by Invitrogen) and the cationic lipid DOTAP LIPOSOMAL TRANSFECTION REAGENT (trade name: manufactured by Roche Applied Science).

As regard to the concentration of the endocytosis inducing substance, the endocytosis inducing substance may be added to a cell suspension before the contacting, such that the final concentration of the endocytosis inducing substance is from 0.1 μM to 20 mM. The concentration (final concentration) of the endocytosis inducing substance added is preferably from 1 μM to 10 mM, from the viewpoint of increasing the incorporation efficiency of aminolevulinic acid into the test cell. The concentration (final concentration) of the endocytosis inducing substance added is more preferably from 5 μM to 2 mM, from the viewpoint of increasing the incorporation efficiency of aminolevulinic acid into the test cells.

The cell membrane protein-stabilizing ion is a substance that can stabilize the structure of a cell adhesion factor present as a cell membrane protein, or a substance that can maintain a transporter for intra- and extracellular substances, such as ATPase, in an activated state.

Examples of the cell membrane protein-stabilizing ion include a Mg ion and a Ca ion.

As regard to the Mg ion, the Mg ion may be added to a cell suspension before the contacting such that the final concentration of the Mg ion is from 0.1 mM to 10 mM. The concentration (final concentration) of Mg ion added is preferably from 0.15 mM to 5 mM, from the viewpoint of increasing the incorporation efficiency of aminolevulinic acid or a derivative thereof into the test cells. The concentration (final concentration) of Mg ion added is more preferably from 0.25 mM to 1 mM, from the viewpoints of increasing the incorporation efficiency of aminolevulinic acid or a derivative thereof into the test cells.

As regard to the Ca ion, the Ca ion may be added to a cell suspension before the contacting such that the final concentration is from 0.1 mM to 10 mM. The concentration (final concentration) of the Ca ion added is preferably from 0.25 mM to 5 mM, from the viewpoint of increasing the incorporation efficiency of aminolevulinic acid or a derivative thereof into the test cells. The concentration (final concentration) of the Ca ion added is more preferably from 0.5 mM to 2 mM, from the viewpoint of increasing the incorporation efficiency of aminolevulinic acid or a derivative thereof into the test cells.

Each of the endocytosis inducing substance and the cell membrane protein stabilizing-ion may be used singly, or in combination of two or more kinds thereof. In view of the stabilization of the cell membrane of the test cells, the Mg ion and the Ca ion may be used in combination.

In the labeling step, the labeling substance is incorporated into the test cells in the peripheral blood-containing sample and the test cells are labeled. The incorporation of the labeling substance may be achieved by maintaining the contact state between the labeling substance and the test cells. Any temperature conditions may be used in the contact state here as long as the test cells can incorporate the labeling substance and labeled with the labeling substance. For example, it may be performed at a temperature condition of from 1° C. to 42° C.

In a case in which the labeling substance is the labeled sugar, the incorporation step and the labeling step may be conducted at a temperature of from 1° C. to 42° C., in view of detection sensitivity of a cancer cell. It is preferable that the incorporation step and the labeling step may be conducted at a temperature of from 2° C. to 40° C., from the viewpoints of improving the detection sensitivity of a cancer cell and reducing the false-positive rate. It is more preferable that the incorporation step and the labeling step may be conducted at a temperature of from 4° C. to 37° C., from the viewpoints of improving the detection sensitivity of a cancer cell and reducing the false-positive rate.

In a case in which the labeling substance is the labeled amino acid, the incorporation step and the labeling step may be conducted at a temperature of from 1° C. to 42° C., in view of detection sensitivity of a cancer cell. It is preferable that the incorporation step and the labeling step may be conducted at a temperature of from 2° C. to 40° C., from the viewpoints of improving the detection sensitivity of a cancer cell and reducing the false-positive rate. It is more preferable that the incorporation step and the labeling step may be conducted at a temperature of from 4° C. to 37° C., from the viewpoints of improving the detection sensitivity of a cancer cell and reducing the false-positive rate.

In a case in which the labeling substance is aminolevulinic acid or a derivative thereof, the incorporation step and the labeling step may be conducted at a temperature of from 30° C. to 42° C., form the viewpoint of detection sensitivity of a cancer cell. It is preferable that the incorporation step and the labeling step may be conducted at a temperature of from 33° C. to 42° C., form the viewpoints of improving the detection sensitivity of a cancer cell and reducing the false-positive rate. It is more preferable that the incorporation step and the labeling step may be conducted at a temperature of from 35° C. to 40° C., form the viewpoints of improving the detection sensitivity of a cancer cell and reducing the false-positive rate.

In a case in which the labeling substance is a combination of the labeled sugar and the labeling amino acid, the incorporation step and the labeling step may be conducted at a temperature of from 1° C. to 42° C., from the viewpoint of detection sensitivity of a cancer cell. It is preferable that the incorporation step and the labeling step may be conducted at a temperature of from 2° C. to 40° C., form the viewpoints of improving the detection sensitivity of a cancer cell and reducing the false-positive rate. It is more preferable that the incorporation step and the labeling step may be performed at a temperature of from 4° C. to 37° C., from the viewpoints of improving the detection sensitivity of a cancer cell and reducing the false-positive rate.

Any duration of the contact time can be used as long as the test cells can incorporate the labeling substance and metabolize the labeling substance therein as needed, and produce a difference between the degree of labeling of a normal cell with the labeling substance and the degree of labeling of a cancer cell with the labeling substance. For example, the contact time may be from 1 minute to 5 hours. The contact time is preferably from 2 minutes to 120 minutes, from the viewpoints of improving the detection sensitivity of a cancer cell and reducing the false-positive rate. The contact time is more preferably from 3 minutes to 90 minutes, from the viewpoints of improving the detection sensitivity of a cancer cell and reducing the false-positive rate.

In a case in which the labeling substance is the labeled sugar, the contact time may be from 1 minute to 2 hours in view of detection sensitivity of a cancer cell. The contact time is preferably from 2 minutes to 60 minutes, from the viewpoints of improving the detection sensitivity of a cancer cell and reducing the false-positive rate. The contact time is more preferably from 3 minutes to 30 minutes, from the viewpoints of improving the detection sensitivity of a cancer cell and reducing the false-positive rate.

In a case in which the labeling substance is the labeled amino acid, the contact time may be from 1 minute to 2 hours, from the viewpoint of detection sensitivity of a cancer cell. The contact time is preferably from 2 minutes to 60 minutes, from the viewpoints of improving detection sensitivity of a cancer cell and reducing the false-positive rate. The contact time is more preferably from 3 minutes to 30 minutes, from the viewpoints of improving the detection sensitivity of a cancer cell and reducing the false-positive rate.

In a case in which the labeling substance is aminolevulinic acid or a derivative thereof, the contact time may be from 10 minutes to 5 hours, from the viewpoint of detection sensitivity of a cancer cell. The contact time is preferably from 15 minutes to 120 minutes, from the viewpoints of improving the detection sensitivity of a cancer cell and reducing the false-positive rate. The contact time is more preferably from 30 minutes to 90 minutes, from the viewpoints of improving the detection sensitivity of a cancer cell and reducing the false-positive rate. In a case in which the labeling substance is aminolevulinic acid or a derivative thereof, the "contact time" needs to be long enough for the test cells to incorporate the labeling substance and metabolize the labeling substance therein, and produce a difference between the degree of labeling of a normal cell with the labeling substance and the degree of labeling of a cancer cell with the labeling substance.

In a case in which the labeling substance is a combination of the labeled amino acid and the labeled amino acid, the contact time may be from 1 minute to 2 hours, from the viewpoint of detection sensitivity of a cancer cell. The contact time is preferably from 2 minutes to 60 minutes, from the viewpoints of improving the detection sensitivity of a cancer cell and reducing the false-positive rate. Further, more preferably, for example, the contact time is more preferably from 3 minutes to 30 minutes, from the viewpoints of improving the detection sensitivity of a cancer cell and reducing the false-positive rate.

In a case in which the labeling substance is the labeled sugar, the final concentration of the labeled sugar may be from 0.01 mM to 100 mM, the contact time may be from 1 minute to 2 hours, and the contact temperature may be from 1° C. to 42° C. It is preferable that the final concentration of the labeled sugar is from 0.05 mM to 75 mM, the contact time is from 2 minutes to 60 minutes, and the contact temperature is from 2° C. to 40° C., in view of detection sensitivity of a cancer cell. It is more preferable that the final concentration of the labeled sugar is from 0.1 mM to 50 mM, the contact time is from 3 minutes to 30 minutes, and the contact temperature is from 4° C. to 37° C., in view of detection sensitivity of a cancer cell.

In a case in which the labeling substance is the labeled amino acid, the final concentration of the labeled amino acid may be from 0.1 μM to 100 mM, the contact time may be from 1 minute to 2 hours, and the contact temperature may be from 1° C. to 42° C. It is preferable that the final concentration of the labeled amino acid is from 0.5 mM to 50 mM, the contact time is from 2 minutes to 60 minutes, and the contact temperature is from 2° C. to 40° C., in view of detection sensitivity of a cancer cell. It is more preferable that the final concentration of the labeled amino acid is from 1 μM to 10 mM, the contact time is from 3 minutes to 30 minutes, and the contact temperature is from 4° C. to 37° C., in view of detection sensitivity of a cancer cell.

In a case in which the labeling substance is aminolevulinic acid or a derivative thereof, the final concentration of aminolevulinic acid or a derivative thereof may be from 0.01 mM to 100 mM, the contact time may be from 10 minute to 5 hours, and the contact temperature may be from 30° C. to 42° C. It is preferable that the final concentration of aminolevulinic acid or a derivative thereof is from 0.05 mM to 50 mM, the contact time is from 15 minutes to 120 minutes, and the contact temperature is from 33° C. to 42° C., in view of detection sensitivity of a cancer cell. It is more preferable that the final concentration of aminolevulinic acid or a derivative thereof is from 0.1 mM to 10 mM, the contact time is from 30 minutes to 90 minutes, and the contact temperature is from 35° C. to 40° C., in view of detection sensitivity of a cancer cell.

In a case in which the labeling substance is a combination of the labeled sugar and the labeled amino acid, the final concentration of the labeled sugar and the labeled amino acid may be from 0.1 μM to 100 mM, the contact time may be from 1 minute to 2 hours, and the contact temperature may be from 1° C. to 42° C. It is preferable that the final concentration of the labeled sugar and the labeled amino acid is from 0.5 μM to 75 mM, the contact time is from 2 minutes to 60 minutes, and the contact temperature is from 2° C. to 40° C., in view of detection sensitivity of a cancer cell. It is more preferable that the final concentration of the labeled sugar and the labeled amino acid is from 1 μM to 50 mM, the contact time is from 3 minutes to 30 minutes, and the contact temperature is from 4° C. to 37° C., in view of detection sensitivity of a cancer cell.

In the detection step, a cell showing a higher degree of labeling with the labeling substance than that shown by a normal cell is detected as a cancer cell.

The metabolic rate of a cancer cell is thought to be 3 to 8 times higher than that of a normal cell among the test cells, and therefore the cancer cell incorporates larger amount of the labeling substance than the normal cell. Furthermore, the degree of labeling is different between cancer cells and normal cells, since cancer cells have a different metabolic pathway than that of normal cells. Therefore, in the detection step, a cell showing a higher degree of labeling with the labeling substance than that shown by a normal cell is distinguished from the normal cell and detected as a cancer cell. In this way, the presence of a cancer cell among the peripheral blood cells can be determined.

The degree of labeling with the labeling substance may be determined depending on the type of label in the labeling substance. For example, in a case in which the label is an enzyme, a degree of coloring developed by adding a substrate for the enzyme to react may be used as the degree of labeling with the labeling substance. Further, in a case in which the label is the fluorescent substance, the degree of labeling with the labeling substance may be a fluorescence intensity obtained by allowing the labeling substance to be incorporated into the test cells and optionally metabolized therein to prepare the sample, and irradiating the sample with excitation light.

The detection of a cancer cell based on the degree of coloring or fluorescence intensity may be performed by visual inspection. Alternatively, the detection may be performed based on a value obtained by measuring the absorbance or fluorescence intensity.

In the detecting method according to the invention, a cell showing a higher degree of labeling with the labeling substance than that shown by a normal cell is detected as a cancer cell. In view of reliable detection of a cancer cell, the detection of the cell may be the detection of the fluorescence intensity of the test cells labeled with the fluorescent substance.

In view of precision detection of a cancer cell, the detection of the cell may be at least one selected from the group consisting of detection of the mean fluorescence intensity of the test cells labeled with the fluorescent substance and detection of the total fluorescence intensity of the fluorescent substance.

In addition to the above detections, the detection of the cell may be performed on the basis of a size of the test cells labeled with the fluorescent substance, from the viewpoint of removing noise or platelets easily. More specifically, the detection may be performed by extracting, as an object, a set of light spots labeled with the labeling substance in which the set may have a diameter larger than 1 μm to 10 μm, preferably larger than 2 μm to 9 μm, and more preferably larger than 3 μm to 8.5 μm.

When the labeled sugar is used as the labeling substance for the detection method according to the invention, a cell that incorporates a higher amount of the labeling substance than that shown by a normal cell can be detected as a cancer cell. In order to reliably detect a cancer cell, in the cell detection, a cell that incorporates preferably at least twice as much as, more preferably at least 3 times as much as, and even more preferably at least 5 times as much as the amount of the labeled sugar incorporated by a normal cell is detected as a cancer cell.

The degree of labeling of a normal cell in peripheral blood with the labeling substance may be determined based on a cell normally present in the peripheral blood of a healthy subject. In a case in which the degree of labeling with the labeling substance under the same conditions is already known in the literature or the like, those literature values may be used.

A normal cell in peripheral blood means a non-cancer cell that is usually present in the peripheral blood of a healthy subject, and examples thereof include erythrocytes, leucocytes (lymphocytes, monocytes, granulocytes), platelets, vascular endothelial cells, vascular endothelial cell precursors, undifferentiated leukocytes, undifferentiated erythrocytes and hematopoietic stem cells. Among these cell types, no significant difference is observed in the degree of labeling with the labeling substance. Therefore, any of these cells may be selected as a normal cell. For example, the degree of labeling of a leucocyte cell may be used as the degree of labeling of a normal cell.

The method for detecting a cancer cell according to the invention may also include isolating the detected cancer cell. This can provide a sample, for example, for further examining a state and type of the detected cancer cell.

As a method for isolating the detected cancer cell, an isolation method depending on the type of the labeling substance may be selected, or an isolation method not limited by the type of the labeling substance may be selected. In a case in which the labeling substance is labeled with a fluorescent substance, the isolation method depending on the type of the labeling substance may be a method known in the art such as a method using a cell sorter, which separates cells based on fluorescence intensity. The isolation method not limited by the type of the labeling substance may be an isolation method on the basis of a size or shape of a cell.

In the method for detecting a cancer according to the invention, a cancer cell in the peripheral blood sample can be efficiently detected as described above. Further, in the method for detecting a cancer, a cancer cell in the peripheral blood sample can be detected with good sensitivity. For example, a cancer cell may be appropriately detected in a sample having a cancer cell density of from 0.01 cells/mL to 10,000 cells/mL, preferably from 0.05 cells/mL to 5,000 cells/mL, and more preferably from 0.1 cells/mL to 1,000 cells/mL.

The method for detecting a cancer cell according to the invention may be conducted with an image analysis system. The image analysis system may include a computer including CPU, ROM that stores a program for executing the image analysis processing routine described below, RAM that temporarily stores data and a storage device such as HDD.

Figure 2:
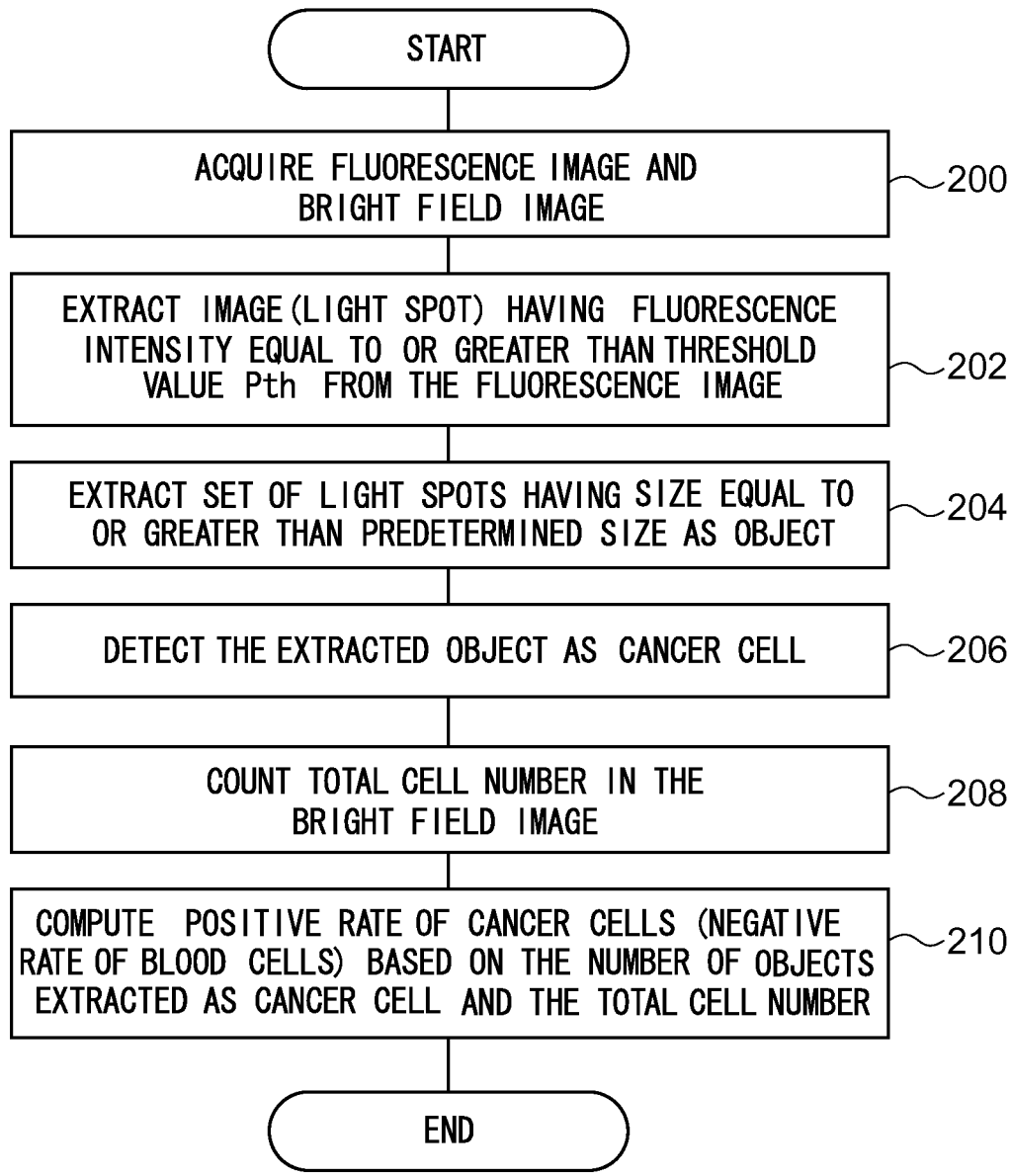
FIG. 2 is a flow chart illustrating another example of the contents of an image processing procedure according to an embodiment of the invention.
Figure 3:
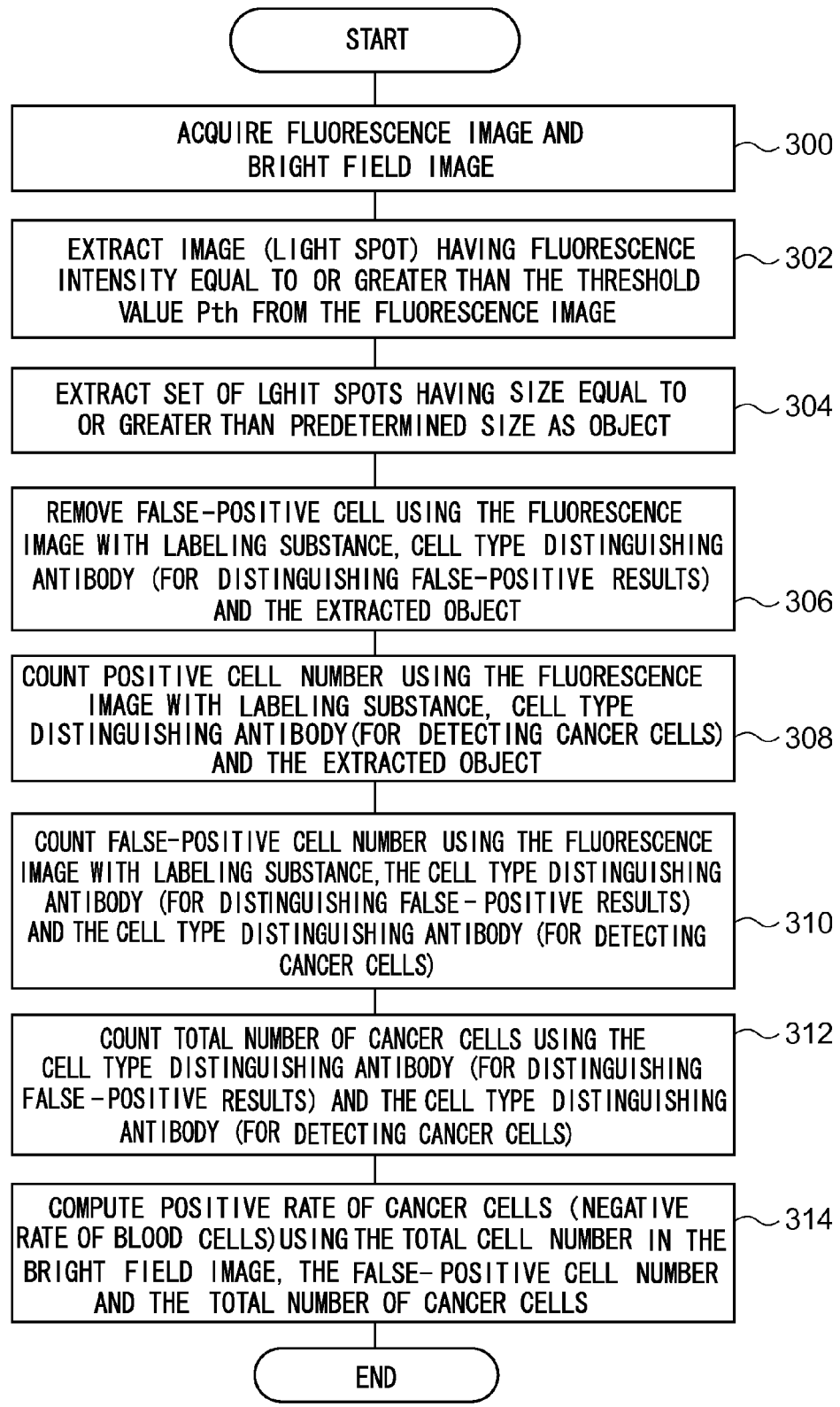
FIG. 3 is a flow chart illustrating another example of the contents of an image processing procedure according to an embodiment of the invention.

Hereinbelow, the operation of the image analysis system using the invention is described. For the same field of the peripheral blood-containing sample including the test cells, a fluorescence image and a bright-field image are captured, and then the image analysis processing routines shown in FIGS. 1, 2 and 3 are executed by the image analysis system.

At step 100, acquisition of the fluorescence image and bright-field image captured is made. Then at step 102, a pixel (a light spot) showing a fluorescence intensity (a luminance value) equal to or greater than the predetermined threshold value Pth is extracted from the fluorescence image acquired at step 100. At this step, noise is removed from the fluorescence image. The threshold value Pth is set at a value appropriate for removing noise in advance depending on the range of luminance values or the like. The threshold value Pth may be set at a fluorescence intensity of from 100 to 3,000, preferably from 150 to 2,500, more preferably from 180 to 2,200.

At step 104, a set of light spots that are equal to or larger than the predetermined size is extracted as an object, which is the set of light spots connecting neighboring light spots extracted at step 102. Further, each of the extracted objects is numbered with an identification number to identify each object. For example, determination as to whether or not the set of light spots has a predetermined size is made by determining whether or not the diameter of the set of light spots is equal to or larger than the predetermined threshold value Rth. In consideration of a magnification of the image, the threshold value Rth may be set with reference to the size of a cell indicated by the set of light spots. The threshold value Rth may be set at a length on the image corresponding to from 1 μm to 10 μm, preferably from 2 μm to 9 μm, more preferably from 3 μm to 8.5 μm. However, it is not limited to the case in which determination is made based on the diameter of the set of light spots, and determination as to whether or not it has a predetermined size may be determined by determining whether or not a number of pixels contained in the set of light spots is equal to or greater than the predetermined number.

Next, at step 106, the mean fluorescence intensity is computed by dividing the sum of the fluorescence intensity of each pixel contained in each object extracted at step 104 by the number of pixels contained in each object.

Then, at step 108, detection threshold value a for detecting a cancer cell is set with reference to the mean fluorescence intensity of each object computed at step 106. For example, the detection threshold value a may be set at a mean or minimum value of the mean fluorescence intensity of each object, and may be set at from 100 to 3,000, preferably from 150 to 2,500, and more preferably from 180 to 2,200.

Then, at step 110, an object having a mean fluorescence intensity equal to or greater than the detection threshold value a set at step 108 is detected as a cancer cell, and the number of the cancer cells is counted.

Then, at step 112, the total number of cells in the bright-field image acquired at step 100 is counted.

Then, at step 114, the positive rate of cancer cells or the negative rate of blood cells is computed based on the number of objects extracted as a cancer cell counted at step 110 and the total number of cells counted at step 112, and the image analysis processing routine is ended.

Note that explanation is given of a case in which the mean fluorescence intensity of each object is computed at step 108. However, the total fluorescence intensity, which is the sum of the fluorescence intensity of each pixel contained in each object, may be computed at step 108.

Hereinbelow, with regard to a case in which only cancer cells or only a peripheral blood-containing sample from a healthy subject is used (i.e., a case in which all the cells extracted from the bright-field image are cancer cells or a peripheral blood-containing sample from a healthy subject), exemplary results of the positive rate of cancer cells and the negative rate of blood cells computed by the above image analysis processing are shown in Table 1.

Alternatively, the image analysis processing routine shown in FIG. 2 is executed as a method that does not include a step corresponding to step 108 for setting the threshold value a to detect a cancer cell.

At step 200, acquisition of the fluorescence image and bright-field image captured is made. Then, at step 202, a pixels (light spot) showing a fluorescence intensity (a luminance value) equal to or greater than the predetermined threshold value Pth is extracted from the fluorescence image acquired at step 200. At this step, noise is removed from the fluorescence image. The threshold value Pth is set at a value appropriate for removing noise in advance depending on the range of luminance values or the like. The threshold value Pth may be set at a fluorescence intensity of from 100 to 2,000, preferably from 150 to 1,500, more preferably from 180 to 1,000.

Then at step 204, a set of light spots that are equal to or larger than the predetermined size is extracted as an object, which is the set of light spots connecting neighboring light spots extracted at step 202. Further, each of the extracted objects is numbered with an identification number for identifying each object. For example, determination as to whether or not the set of light spots has a predetermined size is made by determining whether or not the diameter of the set of light spots is equal to or larger than the predetermined threshold value Rth. In consideration of a magnification of the image, the threshold value Rth may be set with reference to the size of a cell indicated by the set of light spots. The threshold value Rth may be set at a length on the image corresponding to from 1 µm to 10 µm, preferably from 2 µm to 9 µm, more preferably from 3 µm to 8.5 µm. However, it is not limited to the case in which determination is made based on the diameter of the set of light spots, and determination as to whether or not the set of light spots has a predetermined size may be made by determining whether or not a number of pixels contained in the set of light spots is equal to or greater than the predetermined number.

Then, at step 206, an object having a mean fluorescence intensity equal to or greater than the detection threshold value a set at step 204 is detected as a cancer cell, and the number of the cancer cell is counted.

Then, at step 208, the total number of the cells in the bright-field image acquired at step 200 is counted.

Then, at step 210, the positive rate of cancer cells or the negative rate of blood cells is computed based on the number of objects extracted as a cancer cell counted at step 206 and the total number of cells counted at step 208, and the image analysis processing routine is ended.

Alternatively, the image analysis processing routine shown in FIG. 3 is executed as a method that does not include a step corresponding to step 108 for setting the threshold value a to detect a cancer cell.

At step 300, acquisition of the bright-field image, the fluorescence image using a labeling substance, the fluorescence image using a cell type-distinguishing antibody (for distinguishing false-positive results) and the fluorescence image using a cell type-distinguishing antibody (for detecting cancer cells) captured is made. Then, at step 302, a pixel (a light spot) showing a fluorescence intensity (a luminance value) equal to or greater than the predetermined threshold value Pth is extracted from the fluorescence image using a labeling substance acquired at step 300. At this step, noise is removed from the fluorescence image. Threshold value Pth is set at a value appropriate for removing in advance depending on the range of luminance values or the like. The threshold value Pth may be set at a fluorescence intensity of from 100 to 2,000, preferably from 150 to 1,500, more preferably from 180 to 1,000.

Then at step 304, a set of light spots that are equal to or greater than the predetermined size is extracted as an object, which is the set of light spots connecting neighboring light spots extracted at step 302. For example, determination as to whether or not the set of light spots has a predetermined size is made by determining whether or not the diameter of the set of light spots is equal to or larger than the predetermined threshold value Rth. In consideration of a magnification of the image, the threshold value Rth may be set with reference to the size of a cell indicated by the set of light spots. The threshold value Rth may be set at a length on the image corresponding to from 1 µm to 10 µm, preferably from 2 µm to 9 µm, more preferably from 3 µm to 8.5 µm. However, it is not limited to the case in which determination is made based on the diameter of the set of light spots, and determination as to whether or not the set of light spots has a predetermined size may be made by determining whether or not a number of pixels contained in the set of light spots is equal to or greater than the predetermined number.

Then, at step 306, the fluorescence image using a labeling substance and the fluorescence image using a cell type-distinguishing antibody (for distinguishing false-positive results) are superimposed, and among the objects obtained at step 304, a cell exhibiting fluorescence in the both fluorescence images is removed as a false-positive cell from the positive cells. Then, at step 308, the fluorescence image using a labeling substance and the fluorescence image using another cell type-distinguishing antibody (for detecting cancer cells) are superimposed, and among the objects set at step 304, a cell exhibiting fluorescence in the both fluorescence images is counted as a positive cell. Then, at step 310, the fluorescence image using a labeling substance, the fluorescence image using a cell type-distinguishing antibody (for detecting cancer cells) and the fluorescence image using another cell type-distinguishing antibody (for distinguishing false-positive results) are superimposed, and a cell exhibiting fluorescence only in the fluorescence image using a labeling substance is counted as a false-positive cell. Then, at step 312, the fluorescence image using a cell type-distinguishing antibody (for detecting cancer cells) and the fluorescence image using another cell type-distinguishing antibody (for distinguishing false-positive results) are superimposed, and a cell showing fluorescence only in the cell type-distinguishing antibody (for detecting cancer cells) is counted to give a total number of cancer cells.

Then, at step 314, the positive rate of cancer cells or the false-positive rate of blood cells is computed based on the total number of the cells in the bright-field image acquired at step 300, the number of false-positive cells counted at step 310, the number of positive cells counted at step 308 and the total number of cancer cells counted at step 312, and the image analysis processing routine is ended.

TABLE 1

| Conditions | Bright-field counts | Fluorescence intensity counts | Positive rate of cancer cells | Threshold value |
|---|---|---|---|---|
| Reaction conditions: hemolyzed, 10 µM H-Ala(2-Bacd)-OH, 30 min, 37° C. | | | | |
| Cancer cell data (prostate cancer cell line) | | | | |
| Mean luminance | 276 | 278 | 100.7% | 440 |
| Total luminance | 276 | 271 | 98.2% | 50,000 |
| Blood cell data (fresh blood) | | | | |
| Mean luminance | 219 | 0 | 0.0% | 100.0% |
| Total luminance | 219 | 26 | 11.9% | 88.1% |
| Reaction conditions: hemolyzed, 10 mM 2-NBDG, 5 min, 23° C. | | | | |
| Cancer cell data (fibrosarcoma cell line) | | | | |
| Mean luminance | 54 | 54 | 100.0% | 436 |
| Total luminance | 54 | 49 | 90.7% | 35,000 |
| Blood cell data (fresh blood) | | | | |
| Mean luminance | 189 | 9 | 4.8% | 95.2% |
| Total luminance | 189 | 17 | 9.0% | 91.0% |

As shown in Table 1, in each case in which the mean fluorescence intensity or the total fluorescence intensity is used, a cancer cell can be detected with a higher precision. However, in a case in which the total fluorescence intensity is used, the influence of error due to the size of the extracted object is sometimes large. For example, since a longer exposure is required for capturing a fluorescence image, inconsistent focus during the capture affects the size of the extracted object. In a case in which the mean fluorescence intensity is used, such influence of error due to the size is low and therefore a cancer cell can be detected with a higher precision.

Note that explanation is given of a case in which a program for executing the image analysis processing routine is pre-installed in an image analysis system. However, configuration may also be made such that the program is stored in a CD-ROM and DVD disk, a magneto optical disk, or IC card and loaded from the recording medium when executing the image analysis processing. Configuration may also be made such the program is downloaded from a device such as a server connected to a network. It is also possible to implement the above image analysis system by a semiconductor integrated circuit such as ASIC (Application Specific Integrated Circuit).

The cancer cell detection kit according to the invention may contain the labeling substance, as well as a washing solution, a hemolyzing reagent and the peripheral blood sample diluting solution required for the method for detecting a cancer cell according to the invention. The kit may further include additional reagent.

Examples of the additional reagent include substances for improving the specificity of an antibody such as blocking reagents for various receptors; substances to reduce false-positive rate such as iron ions; substances for improving the stability of iron ions such as reducing agents; substances for improving the stability of a cell membrane protein such as Mg ions and Ca ions; and substances for promoting the incorporation of substances into a cell such as endocytosis inducers.

The cancer cell detection kit according to the invention may contain the labeling substance and an explanatory leaflet that explains the cancer cell detection method based on the degree of labeling with the labeling substance.

According to the cancer cell detection kit, a cancer cell in a peripheral blood sample can be detected rapidly and simply. The cancer cell detection method described in the explanatory leaflet of the kit may include entire descriptions of the above method for detecting a cancer cell.

EXAMPLES

Hereinbelow, the invention is described in detail by reference to Examples, but the scope of the invention is not limited to these Examples. Unless otherwise specified, "parts" means "parts by mass".

Example 1

From venous blood of a healthy person, a blood serum sample and precipitates were separated by centrifugation according to the conventional method. From the blood serum sample, a leucocyte layer and an erythrocyte layer were partially collected, and then resuspended in PBS to prepare a leucocyte sample and a erythrocyte sample, respectively.

Breast cancer cell line MCF-7 (purchased from DS Pharma Biomedical Co., Ltd). was cultured at 37° C. with 5% (v/v) $CO_2$ using α-MEM culture medium (Invitrogen, supplemented with 10% (v/v) FBS, 2 mM L-glutamine, 100 U/mL penicillin and 100 µg/mL streptomycin). Immediately before the test, the cells were harvested with 0.25% trypsin-EDTA and washed with PBS, thereby preparing a cancer cell line sample.

To each of 300 µL ($4 \times 10^5$ cells/mL) of the cancer cell line, the blood cells (leucocytes and erythrocytes) or a mixture thereof was added 30 µL of 10 mM 2-[N-(7-nitrobenz-2-oxa-1,3-diazol-4-yl)amino]-2-deoxy-D-glucose (2-NBDG) (Wako Pure Chemical Industries, Ltd.) according to the description in Table 2, thereby preparing samples 1 to 7. These samples were then incubated at 37° C. for 40 minutes. To the sample to which 2-NBDG was not added, a corresponding amount of PBS was added instead of 2-NBDG.

After incubation, each sample was centrifuged at 2,000 rpm for 5 minutes (Hitachi Ltd.) to harvest the cells. To the harvested cells was added 10 µL of an anti-EpCAM antibody-PE (R&D systems), and the mixture was allowed to stand for 30 minutes in the cool and dark place.

After 30 minutes, the mixture was washed with 1,000 µL of PBS, and the cells were harvested by centrifugation at 2000 rpm for 5 minutes in accordance with the conventional method.

The harvested cells were resuspended in 50 µL of PBS, and the entire volume thereof was transferred to a 96-well plate, thereby preparing an observation sample.

Each of the observation samples was observed under a fluorescence microscope (Nikon Corp.), and an amount of 2-NBDG incorporated was visually observed.

Figure 4:
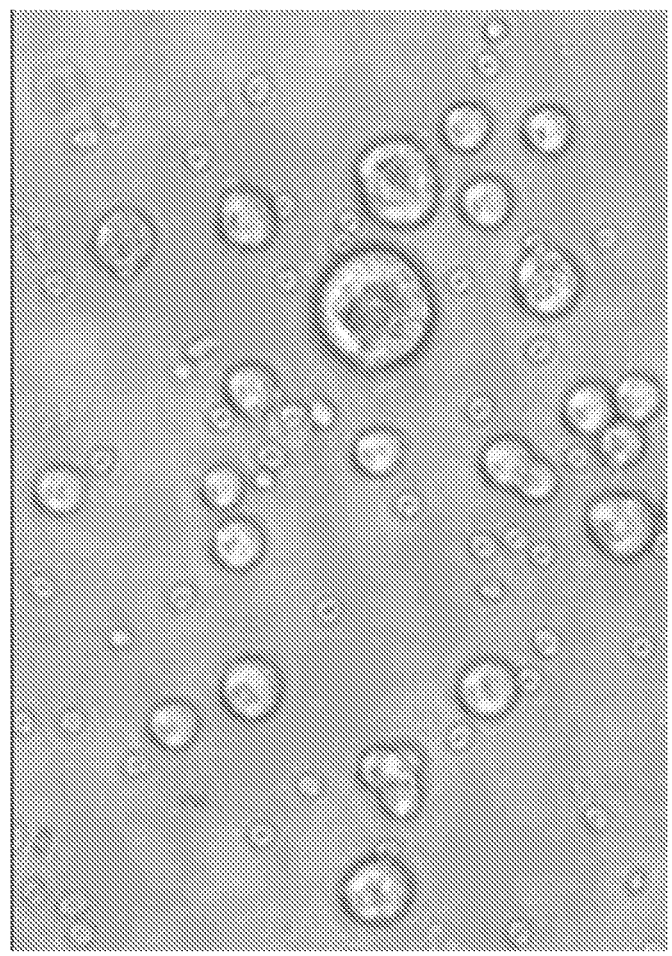
FIG. 4 is a fluorescence micrograph (in phase contrast mode) of the mixture (sample 1) of the cancer cell line and the blood cells according to an embodiment of the invention.
Figure 5:
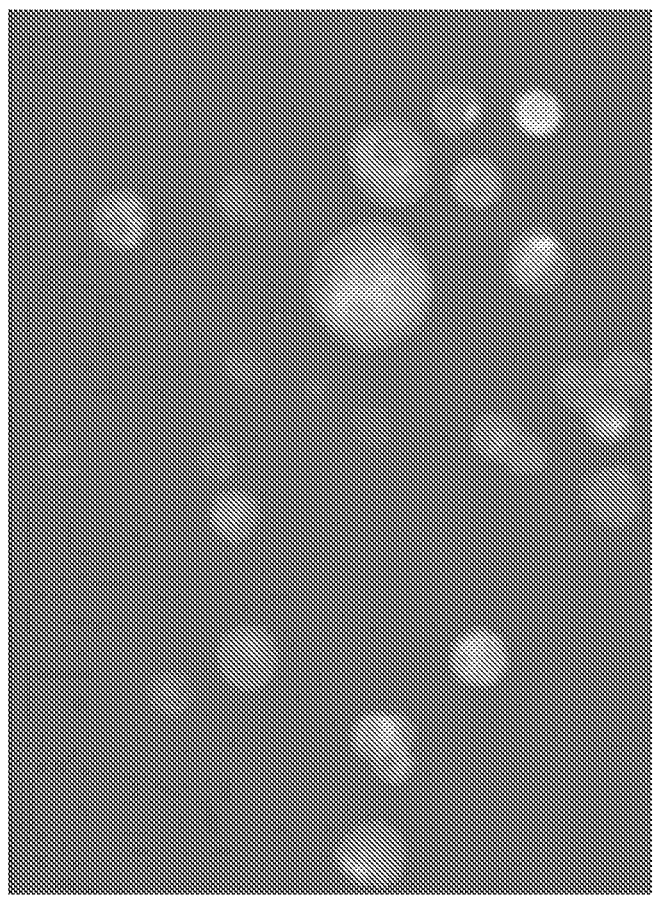
FIG. 5 is a fluorescence micrograph (in fluorescence mode) of sample 1 that incorporates 2-NBDG according to an embodiment of the invention.
Figure 6:
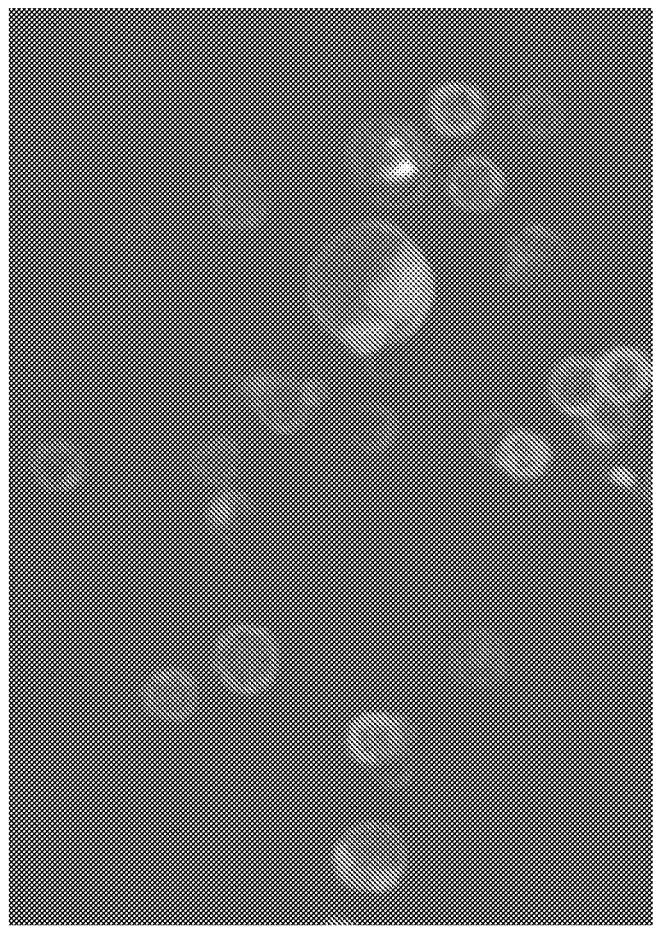
FIG. 6 is a fluorescence micrograph (in fluorescence mode) of sample 1 stained with an anti-EpCAM antibody according to an embodiment of the invention.

Similarly, images stained with the anti-EpCAM antibody-PE were observed to detect a cancer cell. The observation results from sample 1 are shown in FIGS. 4 to 6.

TABLE 2

| | Cell type | | | | |
|---|---|---|---|---|---|
| Sample No. | Cancer cell line | Blood cells | Labeled sugar | Anti-EpCAM antibody | Remarks |
| 1 | Present | Present | Added | Added | Example |
| 2 | Present | — | Added | — | Control |
| 3 | — | Present | — | Added | Control |
| 4 | — | Present | Added | — | Control |
| 5 | Present | — | — | Added | Control |
| 6 | Present | Present | Added | — | Control |
| 7 | Present | Present | — | Added | Control |

In Table 2 above, samples 2 to 7 are controls for ruling out the possibility that the degree of detection of a cancer cell varies depending on so-called experimental techniques. Specifically, sample 2 is a control for assuring that a cancer cell can be detected with the labeled sugar (for ruling out the possibility that the incorporation is inhibited in the presence of the blood cell). Sample 3 is a control for confirming that a blood cell is not stained with an anti-EpCAM antibody. Sample 4 is a control for ruling out the possibility that incorporation of the labeled sugar by a blood cell is affected by mixing operation of the blood cell and the cancer cell. Sample 5 is a control for confirming that a cancer cell can be stained with an anti-EpCAM antibody. Samples 6 and 7 are controls for ruling out the possibility that double labeling of a cancer cell is affected by the presence of a blood cell. The control experiments using these controls ruled out the possibility that the degree of detection of cancer cells varies depending on so-called experimental techniques (data not shown).

Comparative observations in FIGS. 4 to 6 revealed that, in sample 1 in which cancer cell line and blood cells are mixed, 2-NBDG-labeled cells and unlabeled cells are both present (see FIGS. 4 and 5), and that the 2-NBDG-labeled cells are also stained with the anti-EpCAM antibody (see FIG. 6). Therefore, by using 2-NBDG, the cancer cell line in a mixed sample was clearly observed in the fluorescence image.

On the other hand, the leucocyte cell was observed slightly in the fluorescence microscope field, but the signal thereof was much weaker than that of the cancer cell image. The fluorescence intensity of the leucocyte cell image was equal to or less than half the fluorescence intensity of the cancer cell. Since an erythrocyte cell is almost inactive, the fluorescence image thereof was not observed at all.

Therefore, using the peripheral blood sample in which the blood cell and the cancer cell are mixed, the presence of the cancer cell can be detected rapidly and simply based on an amount of a fluorescently-labeled sugar incorporated by the cells.

Example 2

Preparation of Blood Cells

Blood was collected from a human subject using a vacuum blood collection tube (with EDTA·2K). Blood cells were separated using HetaSep (STEMCELL Technologies) in accordance with manufacturer's instructions.

Preparation of Cancer Cells

In accordance with the conventional method, cultured human fibrosarcoma cell line HT1080 (DS Pharma Biomedical Co., Ltd.) was harvested with trypsin (Invitrogen). The human gastric cancer cell line SNU-1 (ATCC), which is a suspension cell line, was directly harvested without any trypsin treatment. The cell suspension of the harvested cancer cells was centrifuged, and the supernatant was removed. The cells were resuspended with Dulbecco's PBS (−) (Nissui Pharmaceutical Co., Ltd.) and centrifuged, and the supernatant was removed again.

When performing the hemolyzing treatment, the blood cell fraction collected as described above was hemolyzed using ammonium chloride (STEMCELL Technologies) according to the manufacture's manuals.

Staining

The number of the cells was counted for each cell line using a hemacytometer in accordance with the conventional method, and then $10^5$ to $10^6$ cells per sample (cell suspension) was aliquoted. Each of the sample was centrifuged to remove the supernatant. Subsequently, 2-NBDG (Wako Pure Chemical Industries, Ltd.; at the final concentration given in Table 3 or 4) dissolved in Dulbecco's PBS (−) was added thereto, and the cells were suspended well. The mixture was then reacted (cultured) at a temperature and time given in Table 3 or 4. After the reaction, Dulbecco's PBS (−) was added to the mixture, and the resultant was centrifuged to remove the supernatant. The cells were resuspended with Dulbecco's PBS (−) and centrifuged, and the supernatant was removed again. The steps of resuspending cells with Dulbecco's PBS (−), centrifuging and removing the supernatant were then repeated 2 to 3 times, thereby washing the cells thoroughly. The cells were resuspended with Dulbecco's PBS (−), the concentration thereof was adjusted, and then added dropwise to a 384-well plate. The plate was centrifuged to spin down the cells. The image was captured with a fluorescence microscope (Nikon Corp.) using B-2A filter combination (Nikon Corp.). The B-2A set covers the following wavelengths. EX (excitation wavelength): 475±15 nm, DM: 505 nm or longer, BA (fluorescence wavelength) 520 nm or longer.

The acquired images were analyzed using an image analysis software NIS-ELEMENTS (trade name, Nikon Corp.) to evaluate the fluorescence intensity of the cell.

The results are shown in Tables 3 and 4. Table 3 shows the results using the peripheral blood samples with the hemolyzing treatment described above, and Table 4 shows the results using the peripheral blood samples without any hemolyzing treatment.

TABLE 3

| | HT1080 cells | | | Blood cells | | | | | |
|---|---|---|---|---|---|---|---|---|---|
| Conditions | Number of cells (bright-field) | Number of cells (fluorescence) | Positive rate | Number of cells (bright-field) | Number of cells (fluorescence) | Positive rate | Negative rate | Threshold value | Remarks |
| 0.1 mM | 129 | 43 | 33.3% | 125 | 0 | 0.0% | 100.0% | 380 | Temperature: 37° C. |
| 1 mM | 104 | 76 | 73.1% | 188 | 2 | 1.1% | 98.9% | 520 | Time: 30 min |
| 10 mM | 100 | 95 | 95.0% | 193 | 0 | 0.0% | 100.0% | 1150 | |
| 5 min | 106 | 127 | 119.8% | 223 | 2 | 0.9% | 99.1% | 570 | Concentration: |
| 30 min | 154 | 166 | 107.8% | 379 | 1 | 0.3% | 99.7% | 880 | 10 mM |
| 60 min | 69 | 71 | 102.9% | 172 | 5 | 2.9% | 97.1% | 750 | Temperature: 37° C. |
| 4° C. | 124 | 98 | 79.0% | 98 | 0 | 0.0% | 100.0% | 640 | Concentration: |

TABLE 3-continued

| | HT1080 cells | | | Blood cells | | | | | |
| --- | --- | --- | --- | --- | --- | --- | --- | --- | --- |
| Conditions | Number of cells (bright-field) | Number of cells (fluorescence) | Positive rate | Number of cells (bright-field) | Number of cells (fluorescence) | Positive rate | Negative rate | Threshold value | Remarks |
| 23° C. | 196 | 159 | 81.1% | 120 | 1 | 0.8% | 99.2% | 640 | 10 mM |
| 37° C. | 199 | 178 | 89.4% | 137 | 2 | 1.5% | 98.5% | 750 | Time: 5 min |

TABLE 4

| | HT1080 cells | | | Blood cells | | | | | |
| --- | --- | --- | --- | --- | --- | --- | --- | --- | --- |
| Conditions | Number of cells (bright-field) | Number of cells (fluorescence) | Positive rate | Number of cells (bright-field) | Number of cells (fluorescence) | Positive rate | Negative rate | Threshold value | Remarks |
| 0.1 mM | 83 | 43 | 51.8% | 283 | 0 | 0.0% | 100.0% | 280 | Temperature: 37° C. |
| 1 mM | 86 | 77 | 89.5% | 343 | 5 | 1.5% | 98.5% | 330 | Time: 30 min |
| 10 mM | 70 | 63 | 90.0% | 626 | 7 | 1.1% | 98.9% | 450 | |
| 5 min | 136 | 126 | 92.6% | 287 | 4 | 1.4% | 98.6% | 380 | Concentration: |
| 30 min | 70 | 68 | 97.1% | 626 | 7 | 1.1% | 98.9% | 450 | 10 mM |
| 60 min | 125 | 123 | 98.4% | 532 | 47 | 8.8% | 91.2% | 500 | Temperature: 37° C. |
| 4° C. | 79 | 75 | 94.9% | 220 | 2 | 0.9% | 99.1% | 310 | Concentration: |
| 23° C. | 95 | 88 | 92.6% | 341 | 7 | 2.1% | 97.9% | 360 | 10 mM |
| 37° C. | 136 | 138 | 101.5% | 287 | 3 | 1.0% | 99.0% | 390 | Time: 5 min |

These results revealed that when 2-NBDG was used as the labeling substance, the concentration of 2-NBDG added may be from 0.1 mM to 10 mM, the reaction temperature may be from 4° C. to 37° C., the reaction time may be 5 minutes or longer, and the threshold value may be a mean fluorescence intensity of from 280 to 1150. Further, the hemolyzing treatment for removing a large amount of contaminating erythrocytes did not affect the cancer cell, revealing that there was no effect due to the hemolyzing treatment.

Example 3

Preparation of Blood Cells

Blood was collected from a human subject using a vacuum blood collection tube (with EDTA•2K). Blood cells were separated using HetaSep (STEMCELL Technologies) in accordance with manufacturer's instructions.

Preparation of Cancer Cells

In accordance with the conventional method, cultured human prostate cancer cell line PC3 (DS Pharma Biomedical Co., Ltd.) was harvested with trypsin (Invitrogen). The human gastric cancer cell line SNU-1 (ATCC), which is a suspension cell line, was directly harvested without any trypsin treatment. The cell suspension of the harvested cancer cells was centrifuged, and the supernatant was removed. The cells were resuspended with Dulbecco's PBS (−) (Nissui Pharmaceutical Co., Ltd.) and centrifuged, and the supernatant was removed again.

When performing the hemolyzing treatment, the blood cell fraction collected as described above was hemolyzed using ammonium chloride (STEMCELL Technologies) at room temperature according to the manufacture's manuals.

Staining

The number of the cells was counted for each cell line using a hemacytometer in accordance with the conventional method, and then $10^5$ to $10^6$ cells per sample (cell suspension) was aliquoted. The sample was centrifuged to remove the supernatant. Subsequently, H-Ala(2-Bacd)-OH (Watanabe Chemical Industries, Ltd.) was added thereto (at the final concentration given in Table 5 or 6), and the cells were suspended well. The mixture was then reacted (cultured) at a temperature and time given in Table 5 or 6. After the reaction, Dulbecco's PBS (−) was added to the mixture, and the resultant was centrifuged to remove the supernatant. The cells were resuspended with Dulbecco's PBS and centrifuged, and the supernatant was removed again. The steps of resuspending cells with Dulbecco's PBS (−), centrifuging and removing the supernatant were then repeated 2 to 3 times, thereby washing the cells thoroughly. The cells were resuspended with Dulbecco's PBS (−), the concentration thereof was adjusted, and then added dropwise to a 384-well plate. The plate was centrifuged to spin down the cells. The image was captured with a fluorescence microscope (Nikon Corp.) using B-2A filter set (Nikon Corp.). The B-2A set covers the same wavelengths as those in Example 2. The acquired images were analyzed using an image analysis software NIS-ELEMENTS (trade name, Nikon Corp.) to evaluate the fluorescence intensity of the cell.

The results are shown in Tables 5 and 6. Table 5 shows the results using the peripheral blood samples with the hemolyzing treatment described above, and Table 6 shows the result using the peripheral blood samples without any hemolyzing treatment.

TABLE 5

| | PC3 cells | | | Blood cells | | | | | |
| --- | --- | --- | --- | --- | --- | --- | --- | --- | --- |
| Conditions | Number of cells (bright-field) | Number of cells (fluorescence) | Positive rate | Number of cells (bright-field) | Number of cells (fluorescence) | Positive rate | Negative rate | Threshold value | Remarks |
| 1 μM | 383 | 337 | 88% | 199 | 8 | 4% | 96% | 228 | Temperature: |
| 10 μM | 276 | 278 | 101% | 219 | 0 | 0% | 100% | 440 | 37° C. |

TABLE 5-continued

| | PC3 cells | | | Blood cells | | | | | |
| --- | --- | --- | --- | --- | --- | --- | --- | --- | --- |
| Conditions | Number of cells (bright-field) | Number of cells (fluorescence) | Positive rate | Number of cells (bright-field) | Number of cells (fluorescence) | Positive rate | Negative rate | Threshold value | Remarks |
| 100 μM | 223 | 220 | 99% | 125 | 0 | 0% | 100% | 2044 | Time: 30 min |
| 4° C. | 329 | 306 | 93% | 217 | 1 | 0% | 100% | 436 | Concentration: |
| 23° C. | 311 | 296 | 95% | 117 | 0 | 0% | 100% | 421 | 10 μM |
| 37° C. | 323 | 302 | 93% | 170 | 0 | 0% | 100% | 422 | Time: 30 min |
| 5 min | 145 | 142 | 98% | 242 | 0 | 0% | 100% | 480 | Concentration: |
| 30 min | 135 | 137 | 101% | 224 | 4 | 2% | 98% | 403 | 10 μM |
| 60 min | 130 | 116 | 89% | 171 | 0 | 0% | 100% | 540 | Temperature: 37° C. |

TABLE 6

| | PC3 cells | | | Blood cells | | | | | |
| --- | --- | --- | --- | --- | --- | --- | --- | --- | --- |
| Conditions | Number of cells (bright-field) | Number of cells (fluorescence) | Positive rate | Number of cells (bright-field) | Number of cells (fluorescence) | Positive rate | Negative rate | Threshold value | Remarks |
| 1 μM | 428 | 246 | 57% | 248 | 1 | 0% | 100% | 227 | Temperature: |
| 10 μM | 372 | 381 | 102% | 143 | 0 | 0% | 100% | 345 | 37° C. |
| 100 μM | 348 | 333 | 96% | 246 | 0 | 0% | 100% | 1743 | Time: 30 min |
| 4° C. | 569 | 484 | 85% | 275 | 1 | 0% | 100% | 440 | Concentration: |
| 23° C. | 487 | 419 | 86% | 205 | 0 | 0% | 100% | 448 | 10 μM |
| 37° C. | 300 | 277 | 92% | 164 | 0 | 0% | 100% | 452 | Time: 30 min |
| 5 min | 136 | 126 | 93% | 274 | 0 | 0% | 100% | 541 | Concentration: |
| 30 min | 208 | 208 | 100% | 387 | 8 | 2% | 98% | 384 | 10 μM |
| 60 min | 114 | 112 | 98% | 364 | 1 | 0% | 100% | 496 | Temperature: 37° C. |

These results revealed that when H-Ala(2-Bacd)-OH was used as a labeling substance, the concentration of H-Ala(2-Bacd)-OH added may be from 1 μM to 100 μM, the reaction temperature may be from 4° C. to 37° C., the reaction time may be 5 minutes or longer, and the threshold value may be a mean fluorescence intensity of from 227 to 2044. Further, the hemolyzing treatment for removing a large amount of contaminating erythrocytes did not affect the cancer cell, revealing that there was no effect due to the hemolyzing treatment.

Example 4

Preparation of Blood Cells

Blood was collected from a human subject using a vacuum blood collection tube (with EDTA•2K). Blood cells were separated using HetaSep (STEMCELL Technologies) in accordance with manufacturer's instructions.

Preparation of Cancer Cells

In accordance with the conventional method, cultured human prostate cancer cell line PC3 (DS Pharma Biomedical Co., Ltd.) was harvested with trypsin (Invitrogen). The human gastric cancer cell line SNU-1 (ATCC), which is a suspension cell line, was directly harvested without any trypsin treatment. The cell suspension of the harvested cancer cells was centrifuged, and the supernatant was removed. The cells were resuspended with Dulbecco's PBS (+) (Nissui Pharmaceutical Co., Ltd.) and centrifuged, and the supernatant was removed again.

When performing the hemolyzing treatment, the collected blood cell fraction was hemolyzed using ammonium chloride (STEMCELL Technologies) at room temperature according to the manufacture's manuals.

Staining

The number of the cells was counted using a hemacytometer in accordance with the conventional method, and then $10^5$ to $10^6$ cells per sample (cell suspension) was aliquoted. The sample was centrifuged to remove the supernatant. Subsequently, aminolevulinic acid 5-AMINOLEVULINATE HYDROCHLORIDE (trade name, Cosmo Bio Co., Ltd., at the final concentration given in Table 7 or 8) dissolved in Dulbecco's PBS (+) and $FeCl_2$ and ascorbic acid having the same concentration as that of aminolevulinic acid, respectively, were added thereto, and the cells were suspended well. The mixture was then reacted (cultured) at a temperature and time given in Table 7 or 8. The number of the cells was adjusted, and then the cells were added dropwise to a 384-well plate. The plate was centrifuged to spin down the cells. The image was captured with a fluorescence microscope (Nikon Corp.).

The wavelengths for the fluorescence filter set: EX (excitation wavelength): 402±7.5, DM: 430 or longer, BA (fluorescence wavelength): 625±15.

The acquired images were analyzed using an image analysis software NIS-ELEMENTS (trade name, Nikon Corp.) to evaluate the fluorescence intensity of the cell.

The results are shown in Tables 7 and 8. Table 7 shows the result using the peripheral blood samples with the hemolyzing treatment described above, and Table 8 shows the result using the peripheral blood samples without any hemolyzing treatment.

TABLE 7

| Conditions | PC3 cells | | | Blood cells | | | | Remarks |
|---|---|---|---|---|---|---|---|---|
| | Number of cells (bright-field) | Number of cells (fluorescence) | Positive rate | Number of cells (bright-field) | Number of cells (fluorescence) | Positive rate | Negative rate | |
| 0.1 mM | 104 | 46 | 44% | 182 | 3 | 2% | 98% | Temperature: 37° C. |
| 0.3 mM | 85 | 72 | 85% | 227 | 16 | 7% | 93% | Time: 60 min |
| 1 mM | 60 | 53 | 88% | 139 | 18 | 13% | 87% | |
| 4° C. | 87 | 27 | 31% | 206 | 5 | 2% | 98% | Concentration: 0.3 mM |
| 23° C. | 52 | 28 | 54% | 168 | 4 | 2% | 98% | Time: 60 min |
| 37° C. | 41 | 33 | 80% | 121 | 14 | 12% | 88% | |
| 30 min | 133 | 79 | 59% | 130 | 2 | 2% | 98% | Concentration: 0.3 mM |
| 60 min | 109 | 101 | 93% | 197 | 0 | 0% | 100% | Temperature: 37° C. |
| 120 min | 93 | 86 | 92% | 147 | 9 | 6% | 94% | |

TABLE 8

| Conditions | PC3 cells | | | Blood cells | | | | Remarks |
|---|---|---|---|---|---|---|---|---|
| | Number of cells (bright-field) | Number of cells (fluorescence) | Positive rate | Number of cells (bright-field) | Number of cells (fluorescence) | Positive rate | Negative rate | |
| 0.1 mM | 97 | 52 | 54% | 125 | 2 | 2% | 98% | Temperature: 37° C. |
| 0.3 mM | 83 | 73 | 88% | 166 | 2 | 1% | 99% | Time: 60 min |
| 1 mM | 107 | 101 | 94% | 150 | 10 | 7% | 93% | |
| 4° C. | 125 | 16 | 13% | 170 | 4 | 2% | 98% | Concentration: 0.3 mM |
| 23° C. | 123 | 22 | 18% | 254 | 0 | 0% | 100% | Time: 60 min |
| 37° C. | 70 | 58 | 83% | 205 | 1 | 0% | 100% | |
| 30 min | 106 | 85 | 80% | 520 | 10 | 2% | 98% | Concentration: 0.3 mM |
| 60 min | 124 | 101 | 81% | 331 | 3 | 1% | 99% | Temperature: 37° C. |
| 120 min | 107 | 90 | 84% | 340 | 46 | 14% | 86% | |

The results revealed that when aminolevulinic acid was used as a labeling substance, the concentration of aminolevulinic acid added may be from 0.1 mM to 1 mM, the reaction temperature may be from 23° C. to 37° C., and the reaction time may be 30 minutes or longer. Further, the hemolyzing treatment for removing a large amount of contaminating erythrocytes did not affect the cancer cell, revealing that there was no effect due to the hemolyzing treatment.

Example 5

The fluorescence intensity of a cell was evaluated in a manner similar to Example 2, except that 6-NBDG (Invitrogen) was used as the labeling substance instead of using 2-NBDG in the staining of Example 2. The results are shown in Table 9. The final concentrations of 2-NBDG and 6-NBDG are given in Table 9.

These results revealed that not only the glucose having the fluorescent chromophore at the 2-position but also the glucose molecule having the fluorescent chromophore at another position can be used as a labeled sugar.

Example 6

In a manner similar to Example 2, each of human breast adenocarcinoma cells (cell line name: MCF-7; DS Pharma Biomedical Co., Ltd.), human colon adenocarcinoma cells (cell line name: SW620; DS Pharma Biomedical Co., Ltd.), human prostate cancer cells (cell line name: PC3; DS Pharma Biomedical Co., Ltd.), human alveolar epithelial cancer cells (cell line name: NCI-H358; DS Pharma Biomedical Co., Ltd.), human gastric cancer cells (cell line name: SNU-1; ATCC) and human fibrosarcoma cells (cell line name: HT1080; DS Pharma Biomedical Co., Ltd.) was detected with the labeled sugar (2-NBDG).

The results are shown in Table 10. The final concentrations of 2-NBDG and 10-NBDG are given in Table 10.

TABLE 9

| Conditions | Fibrosarcoma cell line | | | Blood cells (fresh blood) | | | | Threshold value |
|---|---|---|---|---|---|---|---|---|
| | Number of cells (bright-field) | Number of cells (fluorescence) | Positive rate | Number of cells (bright-field) | Number of cells (fluorescence) | Positive rate | Negative rate | |
| 2-NBDG | 54 | 54 | 100.0% | 189 | 9 | 4.8% | 95.2% | 370 |
| 6-NBDG (derivative) | 108 | 85 | 78.7% | 109 | 1 | 0.9% | 99.1% | 400 |
| 2-NBDG | 95 | 88 | 92.6% | 341 | 7 | 2.1% | 97.9% | 360 |
| 6-NBDG (derivative) | 128 | 91 | 71.1% | 219 | 2 | 0.9% | 99.1% | 400 |

Reaction conditions: hemolyzed, 10 mM, 5 min, 23° C.
Reaction conditions: not hemolyzed, 10 mM, 5 min, 23° C.

TABLE 10

| Conditions | Cancer cells | | | Blood cells (fresh blood) | | | | |
|---|---|---|---|---|---|---|---|---|
| | Number of cells (bright-field) | Number of cells (fluorescence) | Positive rate | Number of cells (bright-field) | Number of cells (fluorescence) | Positive rate | Negative rate | Threshold value |
| Breast adenocarcinoma | 59 | 59 | 100.0% | 189 | 11 | 5.8% | 94.2% | 330 |
| Colon adenocarcinoma | 81 | 81 | 100.0% | 117 | 4 | 3.4% | 96.6% | 280 |
| Prostate cancer | 63 | 44 | 69.8% | 117 | 0 | 0.0% | 100.0% | 880 |
| Alveolar epithelial cancer | 106 | 88 | 83.0% | 117 | 2 | 1.7% | 98.3% | 370 |
| Gastric cancer | 108 | 54 | 50.0% | 117 | 0 | 0.0% | 100.0% | 490 |
| Fibrosarcoma | 54 | 54 | 100.0% | 189 | 9 | 4.8% | 95.2% | 370 |

Reaction conditions: hemolyzed, 10 mM, 5 min, 23° C.

These results revealed that various types of cancer cells can be detected by using 2-NBDG as the labeling substance.

Example 7

In a manner similar to Example 3, each of human breast adenocarcinoma cells (cell line name: MCF-7; DS Pharma Biomedical Co., Ltd.), human colon adenocarcinoma cells (cell line name: SW620; DS Pharma Biomedical Co., Ltd.), human prostate cancer cells (cell line name: PC3; DS Pharma Biomedical Co., Ltd.), human alveolar epithelial cancer cells (cell line name: NCI-H358; DS Pharma Biomedical Co., Ltd.), human gastric cancer cells (cell line name: SNU-1; ATCC) and human fibrosarcoma cells (cell line name: HT1080; DS Pharma Biomedical Co., Ltd.) was detected with the labeled amino acid.

The results are shown in Table 11. The final concentrations of the labeled amino acid H-Ala(2-Bacd)-OH are given in Table 11.

These results revealed that various types of cancer cells can be detected by using H-Ala(2-Bacd)-OH as the labeling substance.

Example 8

In a manner similar to Example 4, each of human breast adenocarcinoma cells (Cell line name: MCF-7; DS Pharma Biomedical Co., Ltd.), human colon adenocarcinoma cells (Cell line name: SW620; DS Pharma Biomedical Co., Ltd.), human prostate cancer cells (Cell line name: PC3; DS Pharma Biomedical Co., Ltd.), human alveolar epithelial cancer cells (Cell line name: NCI-H358; DS Pharma Biomedical Co., Ltd.), human gastric cancer cells (Cell line name: SNU-1; ATCC) and human fibrosarcoma cells (Cell line name: HT1080; DS Pharma Biomedical Co., Ltd.) was detected with aminolevulinic acid.

The results are shown in Table 12. The final concentrations of aminolevulinic acid are given in Table 12.

TABLE 11

| Conditions | Cancer cells | | | Blood cells (fresh blood) | | | | |
|---|---|---|---|---|---|---|---|---|
| | Number of cells (bright-field) | Number of cells (fluorescence) | Positive rate | Number of cells (bright-field) | Number of cells (fluorescence) | Positive rate | Negative rate | Threshold value |
| Breast adenocarcinoma | 528 | 503 | 95.3% | 219 | 0 | 0.0% | 100.0% | 569 |
| Colon adenocarcinoma | 273 | 66 | 24.2% | 219 | 21 | 9.6% | 90.4% | 285 |
| Prostate cancer | 276 | 278 | 100.7% | 219 | 0 | 0.0% | 100.0% | 440 |
| Alveolar epithelial cancer | 348 | 276 | 79.3% | 219 | 0 | 0.0% | 100.0% | 352 |
| Gastric cancer | 270 | 277 | 102.6% | 219 | 7 | 3.2% | 96.8% | 311 |
| Fibrosarcoma | 268 | 200 | 74.6% | 219 | 42 | 19.2% | 80.8% | 300 |

Reaction conditions: hemolyzed, 10 μM, 30 min, 37° C.

TABLE 12

| Conditions | Cancer cells | | | Blood cells (fresh blood) | | | | |
|---|---|---|---|---|---|---|---|---|
| | Number of cells (bright-field) | Number of cells (fluorescence) | Positive rate | Number of cells (bright-field) | Number of cells (fluorescence) | Positive rate | Negative rate | Threshold value |
| Breast adenocarcinoma | 420 | 364 | 86.7% | 227 | 10 | 4.4% | 95.6% | 268 |
| Colon adenocarcinoma | 469 | 455 | 97.0% | 227 | 11 | 4.8% | 95.2% | 207 |
| Prostate cancer | 109 | 101 | 92.7% | 227 | 11 | 4.8% | 95.2% | 265 |
| Alveolar epithelial cancer | 301 | 284 | 94.4% | 227 | 11 | 4.8% | 95.2% | 212 |
| Gastric cancer | 348 | 284 | 81.6% | 227 | 11 | 4.8% | 95.2% | 198 |
| Fibrosarcoma | 386 | 365 | 94.6% | 227 | 11 | 4.8% | 95.2% | 203 |

Reaction conditions: hemolyzed, 0.3 mM, 60 min, 37° C.

These results revealed that various types of cancer cells can be detected with high sensitivity by using aminolevulinic acid as the labeling substance.

Example 9

Blood was collected from a human subject using a vacuum blood collection tube (with EDTA•2K). Blood cells were separated using HetaSep (STEMCELL Technologies) in accordance with the manufacturer's instructions.

Preparation of Cancer Cells

In accordance with the conventional method, cultured human breast adenocarcinoma cells (cell line name: MCF-7; DS Pharma Biomedical Co., Ltd.), human colon adenocarcinoma cells (cell line name; SW620: DS Pharma Biomedical Co., Ltd.), human prostate cancer cells (cell line name: PC3; DS Pharma Biomedical Co., Ltd.), human alveolar epithelial cancer cells (cell line name: NCI-H358; DS Pharma Biomedical Co., Ltd.) and human fibrosarcoma cells (cell line name: HT1080; DS Pharma Biomedical Co., Ltd.) were harvested with trypsin (Invitrogen). The human gastric cancer cell line SNU-1 (ATCC), which is a suspension cell line, was directly harvested without any trypsin treatment. The cell suspension of the harvested cancer cells was centrifuged, and the supernatant was removed. The cells were resuspended with Dulbecco's PBS (−) (Nissui Pharmaceutical Co., Ltd.) and centrifuged, and the supernatant was removed again.

Hemolyzing Treatment

The blood cell fraction collected as above was hemolyzed using ammonium chloride (STEMCELL TECHNOLOGIES) at room temperature according to the manufacture's manuals.

Staining

The number of the cells was counted using a hemacytometer in accordance with the conventional method, and then $10^5$ to $10^6$ cells per sample (cell suspension) was aliquoted. The sample was centrifuged to remove the supernatant. Subsequently, H-Ala(2-Bacd)-OH (Watanabe Chemical Industries, Ltd.) and 2-NBGD (Wako Pure Chemical Industries, Ltd.) were added thereto (at the final concentration given in Table 13), and the cells were suspended well. The mixture was then allowed to react at 37° C. for 30 minutes. After the reaction, Dulbecco's PBS (−) was added to the mixture, and the resultant was centrifuged to remove the supernatant. The cells were resuspended with Dulbecco's PBS (−) and centrifuged, and the supernatant was removed again. The steps of resuspending with Dulbecco's PBS (−), centrifuging and removing the supernatant were then repeated 2 to 3 times, thereby washing the cells thoroughly. The cells were resuspended with Dulbecco's PBS (−), the concentration thereof was adjusted, and then added dropwise to a 384-well plate. The plate was centrifuged to spin down the cells. The image was captured with a fluorescence microscope (Nikon Corp.) using the B-2A fluorescence filter combination (Nikon Corp.).

The acquired images were analyzed using an image analysis software NIS-ELEMENTS (trade name, Nikon Corp.) to evaluate the fluorescence intensity of the cell. The results are shown in Table 13.

TABLE 13

| | Conditions | Cancer cells | | | Blood cells (fresh blood) | | | | | Remarks |
|---|---|---|---|---|---|---|---|---|---|---|
| | | Number of cells (bright-field) | Number of cells (fluorescence) | Positive rate | Number of cells (bright-field) | Number of cells (fluorescence) | Positive rate | Negative rate | Threshold value | |
| Colon adeno-carcinoma | 2-NBDG single | 81 | 81 | 100.0% | 117 | 4 | 3.4% | 96.6% | 280 | Glucose conc.: 1 mM Amino acid conc.: 10 μM Temp.: 37° C. Time: 30 min |
| | H-Ala(2-Bacd)-OH single | 273 | 66 | 24.2% | 219 | 21 | 9.6% | 90.4% | 285 | |
| | 2-NBDG and H-Ala(2-Bacd)-OH double | 93 | 87 | 93.5% | 177 | 19 | 10.7% | 89.3% | 300 | |
| Gastric cancer | 2-NBDG single | 108 | 54 | 50.0% | 117 | 0 | 0.0% | 100.0% | 490 | |
| | H-Ala(2-Bacd)-OH single | 270 | 277 | 102.6% | 219 | 7 | 3.2% | 96.8% | 311 | |
| | 2-NBDG and H-Ala(2-Bacd)-OH double | 84 | 83 | 98.8% | 177 | 1 | 0.6% | 99.4 | 390 | |

TABLE 13-continued

| | Conditions | Cancer cells | | | Blood cells (fresh blood) | | | | | |
|---|---|---|---|---|---|---|---|---|---|---|
| | | Number of cells (bright-field) | Number of cells (fluorescence) | Positive rate | Number of cells (bright-field) | Number of cells (fluorescence) | Positive rate | Negative rate | Threshold value | Remarks |
| Fibro-sarcoma | 2-NBDG single | 54 | 54 | 100.0% | 189 | 9 | 4.8% | 95.2% | 370 | |
| | H-Ala(2-Bacd)-OH single | 268 | 200 | 74.6% | 219 | 42 | 19.2% | 80.8% | 300 | |
| | 2-NBDG and H-Ala(2-Bacd)-OH double | 90 | 89 | 98.9% | 177 | 1 | 0.6% | 99.4% | 410 | |
| Prostate cancer | 2-NBDG and H-Ala(2-Bacd)-OH double | 131 | 125 | 95.4% | 177 | 1 | 0.6% | 99.4% | 480 | |
| Alveolar epithelial cancer | 2-NBDG and H-Ala(2-Bacd)-OH double | 95 | 98 | 103.2% | 177 | 13 | 7.3% | 92.7% | 320 | |
| Breast adenocarcinoma | 2-NBDG and H-Ala(2-Bacd)-OH double | 114 | 105 | 92.1% | 177 | 19 | 10.7% | 89.3% | 300 | |

These results revealed that by using 2-NBDG and H-Ala(2-Bacd)-OH in combination, and setting the mean fluorescence intensity threshold at from 280 to 490, various types of cancer cells can be detected with high sensitivity, including gastric cancer cells showing a low positive rate when 2-NBDG was used singly and colon cancer cells showing a low positive rate when H-Ala(2-Bacd)-OH was used singly.

Example 10

Preparation of Cells

In accordance with the conventional method, human fibrosarcoma cell HT-1080 (DS Pharma Biomedical Co., Ltd.) and normal human dermal fibroblast cell NHDF (Lonza) in culture were harvested with trypsin (Invitrogen). The cell suspension of the harvested cancer cells was centrifuged, and the supernatant was removed. The cells were then resuspended with Dulbecco's PBS (+) (Nissui Pharmaceutical Co., Ltd.) and centrifuged, and the supernatant was removed again.

Staining

The number of the cells was counted using a hemacytometer in accordance with the conventional method, and then $10^5$ to $10^6$ cells per sample (cell suspension) was aliquoted. The sample was centrifuged to remove the supernatant. In the case an iron ion and a reducing agent were added, 0.3 mM of aminolevulinic acid (trade name: 5-AMINOLEVULINATE HYDROCHLORIDE, Cosmo Bio Co., Ltd.), 0.3 mM of $FeCl_2$ and 0.3 mM of ascorbic acid dissolved in Dulbecco's PBS (+) were added thereto, and the cells were suspended well. In the case an iron ion and a reducing agent were not added, 0.3 mM of aminolevulinic acid dissolved in Dulbecco's PBS (+) was added singly, and the cells were suspended well. Each of the mixture was then allowed to react at 37° C. for 60 minutes. The number of cells was adjusted, and then the cells were added dropwise to a 384-well plate. The plate was centrifuged to spin down the cells.

Capturing Fluorescence

Under a fluorescence microscope (Nikon Corp.), bright-field (10× objective) and fluorescence (10× objective) images of the same filed were observed to examine the degree of false-positive results. The results are shown in Table 14.

The fluorescence filter set: EX (excitation wavelength) 402±7.5, DM 430 or longer, BA (fluorescence wavelength) 625±15.

TABLE 14

| Condition | | | Fibroblast sarcoma cell (HT-1080) | | | Normal epithelial cells (NHDF) | | | | |
|---|---|---|---|---|---|---|---|---|---|---|
| Aminolevulinic acid | Ascorbic acid | $FeCl_2$ | Number of cells (bright-field) | Number of cells (fluorescence) | Positive rate | Number of cells (bright-field) | Number of cells (fluorescence) | Positive rate | Negative rate | Remarks |
| 0.3 mM | 0 | 0 | 146 | 142 | 97.3% | 53 | 33 | 62.3% | 37.7% | Temp.: 37° C. |
| 0.3 mM | 0.3 mM | 0.3 mM | 135 | 107 | 79.3% | 91 | 13 | 14.3% | 85.7% | Time: 60 min |

These results revealed that when aminolevulinic acid was used in combination with $FeCl_2$ and ascorbic acid, the false-positive rate can be reduced.

Example 11

Preparation of Cells

In accordance with the conventional method, human breast adenocarcinoma cells (cell line name: MCF-7; DS Pharma Biomedical Co., Ltd.) in culture was harvested with trypsin (Invitrogen). The cancer cell suspension harvested was centrifuged, and the supernatant was removed. The cells were resuspended with Dulbecco's PBS (+) (Nissui Pharmaceutical Co., Ltd.) and centrifuged, and the supernatant was removed again.

Staining

The number of the cells was counted using a hemacytometer in accordance with the conventional method, and then $2.8 \times 10^5$ cells per sample was aliquoted. The sample was well suspended in Dulbecco's PBS (+) containing Mg ions and Ca ions, to which aminolevulinic acid (trade name: 5-AMINOLEVULINATE HYDROCHLORIDE, Cosmo Bio Co., Ltd.) was added so to have a concentration of 1 mM. The suspension was then allowed to react at 37° C.

Fluorescence Detection

The fluorescence values of the cell suspension were measured using an i-densy (ARKRAY, Inc) at 15 minutes, 30 minutes, 60 minutes and 90 minutes after the start of the reaction. Conditions for fluorescence value measurement are as follows: 40° C. in the temperature regulated and light-intensity mode, Gain "3", LED1 (390±20 nm for excitation)—PD3 (642.5±57.5 nm for detection).

Figure 7:
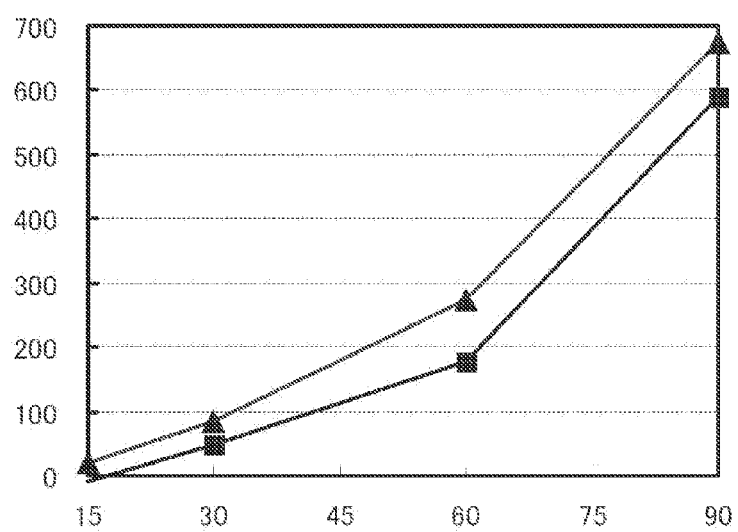
FIG. 7 is a graph illustrating a reactivity of aminolevulinic acid according to an embodiment of the invention.

The results are shown in FIG. 7. In FIG. 7, the vertical axis represents fluorescence values, and the horizontal axis represents the reaction time. The solid squares represent fluorescence values obtained from the sample using Dulbecco's PBS (−) containing no Mg and Ca ions. The solid triangles represent fluorescence values obtained from the sample using Dulbecco's PBS (+) containing Mg and Ca ions. The results shown with solid square were obtained in a manner similar to Example 11, except that Dulbecco's PBS (−) was used instead of using Dulbecco's PBS (+) in Example 11.

These results revealed that when aminolevulinic acid was used in combination with Mg ions and Ca ions, the reactivity of aminolevulinic acid can be improved.

Example 12

Fluorescence values of the cell suspension were measured in a manner similar to Example 11, except that aminolevulinic acid dissolved in Dulbecco's PBS (+) was added to have a concentration of 1 mM, and 10 μM ENDO-PORTER (GeneTools, LLC) was added in the staining in Example 11.

Figure 8:
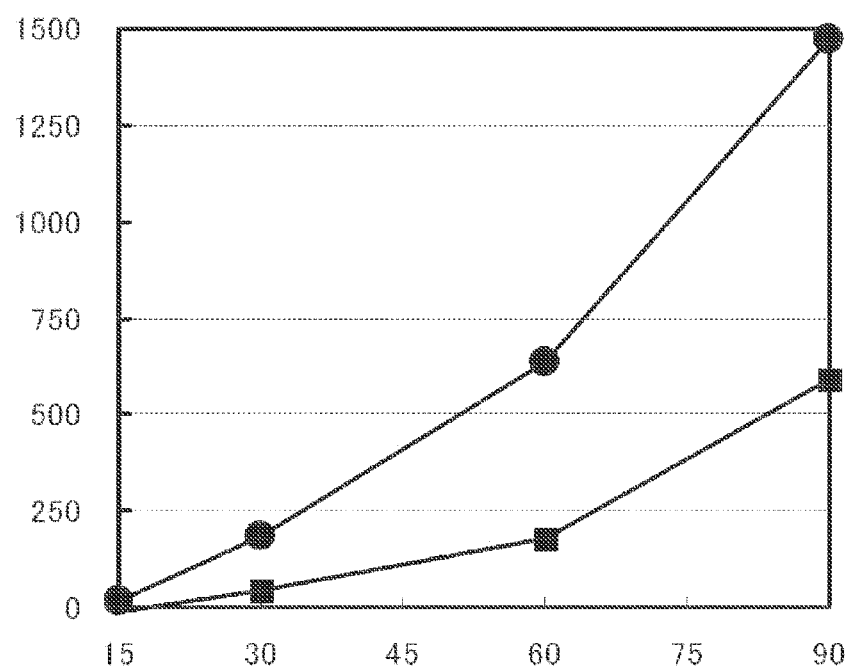
FIG. 8 is a graph illustrating a reactivity of aminolevulinic acid according to an embodiment of the invention.

The results are shown in FIG. 8. In FIG. 8, the vertical axis represents fluorescence values, and the horizontal axis represents the reaction time. The solid squares represent fluorescence values obtained from the sample using Dulbecco's PBS (−) containing no Mg and Ca ions. The solid circles represent fluorescence values obtained from the sample using Dulbecco's PBS (+) containing Mg and Ca ions and supplemented with ENDO-PORTER.

These results revealed that when aminolevulinic acid was used in combination with Mg ions and Ca ions, the addition of ENDO-PORTER further improves the reactivity of aminolevulinic acid.

Figure 9:
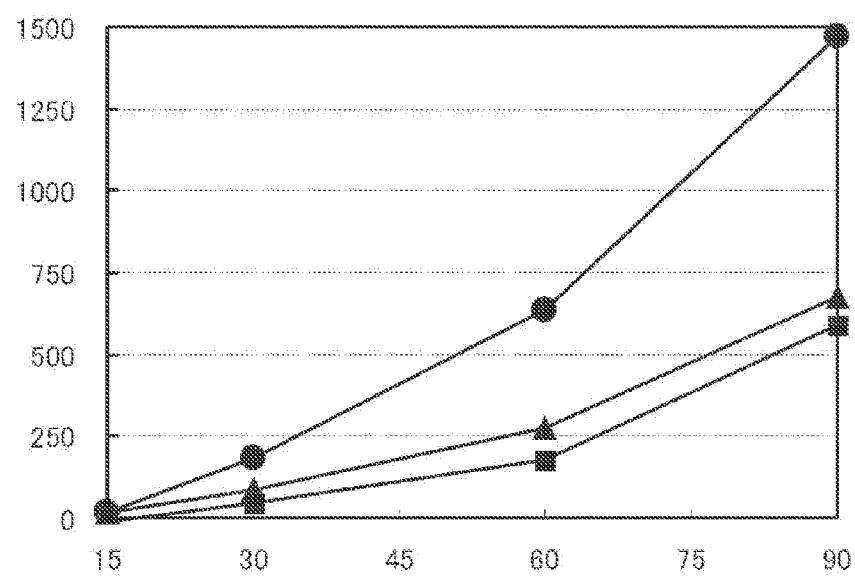
FIG. 9 is a graph illustrating a reactivity of aminolevulinic acid according to an embodiment of the invention.

In FIG. 9, the results from Examples 11 and 12 are summarized. This revealed that as compared with the case in which aminolevulinic acid was added singly (solid triangles), the addition of Mg and Ca ions to aminolevulinic acid (solid squares) improves the reactivity of aminolevulinic acid, and the addition of Mg and Ca ions and ENDO-PORTER to aminolevulinic acid (solid circles) further improves the reactivity of aminolevulinic acid.

Example 13

With regard to the labeling substance, H-Lys(DMACA)-OH (Watanabe Chemical Industries, Ltd.) or H-Glu(EDANS)—OH (Watanabe Chemical Industries, Ltd.) was used instead of using H-Ala(2-Bacd)-OH in the staining of Example 3.

Further, the fluorescence intensity of the cells was evaluated in a manner similar to Example 2, except the fluorescence filter covering the wavelengths of EX (excitation wavelength) of 365/±10, DM of 400 or longer and BA (fluorescence wavelength) of 470±20 was used based on the fluorescent property of the fluorescent substances. The results are shown in Table 15.

TABLE 15

| | | Gastric cancer cell line | | | Blood cells | | | | |
|---|---|---|---|---|---|---|---|---|---|
| Substance type | Concentration | Number of cells (bright-field) | Number of cells (fluorescence) | Positive rate | Number of cells (bright-field) | Number of cells (fluorescence) | Positive rate | Negative rate | Threshold value |
| H-Ala(2-Bacd)-OH | 10 μM | 270 | 277 | 102.6% | 219 | 7 | 3.2% | 96.8% | 311 |
| H-Lys(DMACA)-OH | 1 mM | 316 | 272 | 86.1% | 575 | 102 | 17.7% | 82.3% | 273 |
| H-Glu(EDANS)-OH | 1 mM | 65 | 37 | 56.9% | 159 | 1 | 0.6% | 99.4% | 300 |

Reaction conditions: hemolyzed, 30 min, 37° C.

These results revealed that not only the labeled neutral amino acid H-Ala(2-Bacd)-OH but also other labeled amino acids (such as the labeled basic amino acid H-Lys(DMACA)-OH and the labeled acidic amino acid H-Glu(EDANS)—OH) can be used as the labeled amino acid. It is found that the labeled neutral amino acid H-Ala(2-Bacd)-OH and the labeled acidic amino acid H-Glu(EDANS)—OH show a high selectivity for a cancer cell in view of a negative rate.

Example 14

Preparation of Blood Cells

Blood was collected from a human subject using a vacuum blood collection tube (with EDTA•2K). Blood cells were separated using HetaSep (STEMCELL Technologies) in accordance with the manufacturer's instructions.

Preparation of Cancer Cells

In accordance with the conventional method, cultured human prostate cancer cell line (PC3, DS Pharma Biomedical Co., Ltd.) was harvested with trypsin (Invitrogen). The cell suspension of the harvested cancer cells was centrifuged, and the supernatant was removed. The cells were resuspended with Dulbecco's PBS (+) (Nissui Pharmaceutical Co., Ltd.) and centrifuged, and the supernatant was removed again.

Preparing a Mixture of Blood and Cancer Cells

The number of the cells in the suspension of the isolated blood cells was counted using a hemacytometer in accordance with the conventional method. Further, the number of the cells was also counted for the human prostate cancer cell line (PC3) in a similar manner, and the cells were added to the blood cell suspension to give a cell number of 1% of that of the blood cells. The blood cell suspension to which the human prostate cancer cell line (PC3) was added was hemolyzed at room temperature using ammonium chloride (STEMCELL Technologies) in accordance with the manufacturer's instructions.

Staining

The number of the cells was counted using a hemacytometer in accordance with the conventional method, and then $10^5$ to $10^6$ cells per sample (cell suspension) was aliquoted. The sample was centrifuged to remove the supernatant, 0.3 mM of aminolevulinic acid (trade name: 5-AMINOLEVULINATE HYDROCHLORIDE, Cosmo Bio Co., Ltd.) dissolved in Dulbecco's PBS (+), 0.3 mM of $FeCl_2$ and 0.3 mM of ascorbic acid were added thereto, and the cells were well suspended. The suspension was then reacted (cultured) at 37° C. for 60 minutes. After the reaction, the reactant was centrifuged to remove the supernatant, and FcR Blocking Reagent (Miltenyi Biotec) was added thereto according to the manufacturer's instructions. The mixture was allowed to react at 4° C. for 30 minutes. After the reaction, an FITC-labeled anti-CD45 antibody (Miltenyi Biotec), an FITC-labeled anti CD34-antibody (BioLegend) and a PE labeled anti-EpCAM antibody (Miltenyi Biotec) are added to each according to the package insert, and allowed to react at 23° C. for 30 minutes. After the reaction, Dulbecco's PBS (−) was added thereto, and the mixture was centrifuged to remove the supernatant. The cells were resuspended with Dulbecco's PBS (−) and centrifuged, and the supernatant was removed again. The steps of resuspending with Dulbecco's PBS (−), centrifuging and removing the supernatant were repeated 2 to 3 times, thereby washing the cells thoroughly. The number of cells was adjusted, and then the cells were added dropwise to a 384-well plate. The plate was centrifuged to spin down the cells. The image was captured with a fluorescence microscope (Nikon Corp.). Protoporphyrin IX was detected with the fluorescence filter set 1, the PE-labeled anti-EpCAM antibody was detected with the fluorescence filter set 2, and the FITC-labeled anti-CD45 antibody and the FITC-labeled anti-CD34 antibody were detected with the fluorescence filter set 3.

Wavelengths for the fluorescence filter set 1: EX (excitation wavelength) 402±7.5 nm, DM 430 nm or longer, BA (fluorescence wavelength) 625±15 nm.

Wavelengths for the fluorescence filter set 2: EX (excitation wavelength) 535±25 nm, DM 575 nm or longer, BA (fluorescence wavelength) 590 nm or longer.

Wavelengths for the fluorescence filter set 3: EX (excitation wavelength) 475±15 nm, DM 505 nm or longer, BA (fluorescence wavelength) 525±10 nm.

The acquired images were analyzed using an image analysis software NIS-ELEMENTS (trade name, Nikon Corp.) to evaluate the fluorescence intensity of the cell. The results are shown in Table 16.

TABLE 16

| Conditions | Mixture of blood cells and PC3 cells ||||||
|---|---|---|---|---|---|
| | Total cell number | PC3 cell number (EpCAM positive) | Amino-levulinic acid-positive cell number | Positive cell number (aminolevulinic acid-positive, EpCAM-positive, CD45/CD34-negative) | False-positive cell number (aminolevulinic acid-positive, EpCAM-negative, CD45/CD34-positive) | False-positive cell number (aminolevulinic acid-positive, EpCAM-negative, CD45/CD34-negative) |
| Stained with leukocyte-distinguishing antibody and PC3-distinguishing antibody, in combination with aminolevulinic acid | 2000 | 33 | 49 | 28 | 21 | 0 |

| Conditions | Mixture of blood cells and PC3 cells ||||| |
|---|---|---|---|---|---|
| | Positive rate | False-positive rate (using α-CD45/34) | False-positive rate (without using α-CD45/34) | Threshold value | Remarks |
| Stained with leukocyte-distinguishing antibody and PC3-distinguishing antibody, in combination with aminolevulinic acid | 85% | 0.0% | 1.1% | 216 | ALA: 0.3 mM<br>$FeCl_2$: 0.3 mM<br>Ascorbic acid: 0.3 mM<br>Temp.: 37° C.<br>Time: 60 min<br>leukocyte distinguishing antibody: FITC-α-CD45/CD34 antibody<br>PC3 distinguishing antibody: PE-α-EpCAM antibody |

These results revealed that when aminolevulinic acid was used in combination with an anti-CD34 antibody and an anti-CD45 antibody, the false-positive rate can be reduced.

The disclosure of Japanese Patent Application No. 2010-288936 (filed on Dec. 24, 2010) is herein incorporated by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method for testing a peripheral blood-containing sample for cancer cells, the method comprising:
   contacting in vitro test cells present in the blood-containing sample with a labeling substance under conditions sufficient for the test cells to react with the labeling substance to form labeled test cells,
   wherein the labeling substance is incorporated into the cancer cells and metabolized to protoporphyrin IX, and the following conditions of (i) and (ii) are satisfied:
   (i) contacting in vitro the peripheral blood-containing sample comprising the test cells with the labeling substance in the presence of 0.1 to 10 mM of a Mg ion and/or a Ca ion and at least one selected from the group consisting of a reducing agent and an endocytosis-including substance;
   (ii) the test cells are allowed to incorporate the labeling substance from 15 minutes to 120 minutes,
   wherein the labeling substance is at least one selected from the group consisting of aminolevulinic acid, a salt of aminolevulinic acid, an ester of aminolevulinic acid and a salt of an ester of aminolevulinic acid, and
   wherein the method is sufficiently sensitive to detect a cancer cell in the sample when the sample has a cancer cell density of 0.05 cells/mL to 5,000 cells/mL.

2. The method according to claim 1, wherein the testing includes determining a fluorescence intensity of the test cells labeled with the protoporphyrin IX.

3. The method according to claim 1, wherein the testing includes determining at least one selected from the group consisting of a mean fluorescence intensity and a total fluorescence intensity of the test cells labeled with the protoporphyrin IX.

4. The method according to claim 1, wherein the testing is performed on the basis of size of the test cells labeled with the protoporphyrin IX.

5. The method according to claim 1, wherein the peripheral blood-containing sample is hemolyzed.

6. The method according to claim 1, wherein the contacting in vitro of the peripheral blood-containing sample with the labeling substance is conducted in the presence of 0.1 to 10 mM of the Mg ion and/or the Ca ion and an endocytosis-inducing substance.

7. The method according to claim 1, wherein the reducing agent in the contacting in vitro of the peripheral blood-containing sample with the labeling substance is ascorbic acid.

8. The method according to claim 1, wherein the test cells react with the labeling substance at a temperature of from 1° C. to 42° C.

9. The method according to claim 1, wherein the method further comprises contacting in vitro the test cells present in the peripheral blood containing sample with a cell-type distinguishing antibody.

10. The method according to claim 9, wherein the cell type-distinguishing antibody comprises at least one selected from the group consisting of an anti-CD45 antibody and an anti-CD34 antibody.

* * * * *